(12) United States Patent
Virden

(10) Patent No.: US 12,629,505 B2
(45) Date of Patent: *May 19, 2026

(54) MINIMALLY TRAUMATIC TROCAR METHOD FOR SUBCUTANEOUS MEDICATION DELIVERY

(71) Applicant: Charles P. Virden, Reno, NV (US)

(72) Inventor: Charles P. Virden, Reno, NV (US)

(73) Assignee: VITALTE LIFESCIENCES INC., Reno, NV (US)

( * ) Notice: Subject to any disclaimer, the term of this patent is extended or adjusted under 35 U.S.C. 154(b) by 1066 days.

This patent is subject to a terminal disclaimer.

(21) Appl. No.: 17/588,228

(22) Filed: Jan. 29, 2022

(65) Prior Publication Data

US 2022/0331573 A1     Oct. 20, 2022

Related U.S. Application Data

(63) Continuation-in-part of application No. 16/997,803, filed on Aug. 19, 2020, now Pat. No. 12,042,615, (Continued)

(51) Int. Cl.
*A61M 37/00*       (2006.01)
*A61M 25/00*       (2006.01)

(52) U.S. Cl.
CPC . *A61M 37/0069* (2013.01); *A61M 2025/0042* (2013.01)

(58) Field of Classification Search
CPC ............ A61M 37/0069; A61M 31/007; A61B 17/3468; A61B 17/3203; A61B 2017/3456

See application file for complete search history.

(56) References Cited

U.S. PATENT DOCUMENTS

| | | | | |
|---|---|---|---|---|
| 1,789,766 A | * | 1/1931 | Muir | ................... A61N 5/1007 604/64 |
| 3,491,756 A | | 1/1970 | Bentov | |

(Continued)

FOREIGN PATENT DOCUMENTS

WO        1996001132 A1      1/1996

OTHER PUBLICATIONS

Cavender, Richard K., Surgical Techniques: Subcutaneous Testosterone Pellet Implantation Procedure for Treatment of Testosterone Deficiency Syndrome, J Sex Med 2009; 6:21-24 (Jan. 8, 2009).

(Continued)

*Primary Examiner* — Nilay J Shah
(74) *Attorney, Agent, or Firm* — Kerr IP Group, LLC

(57)        ABSTRACT

A method for delivering a medication pellet to a subcutaneous insertion site with a round tipped obturator and blunt cannula is described. The obturator is received within the cannula. The cannula includes a tubular cannula body having a smooth anterior surface a medication slot disposed along the cannula body. The cannula and obturator probe an incision into the subcutaneous tissue along a non-linear insertion path within the subcutaneous tissue. The obturator is removed from the cannula, and the medication pellet is placed in the medication slot. The cannula body again receives the obturator, which passes the pellet through the cannula body with its anterior rounded tip so that the obturator pushes the pellet(s) through the cannula body. The pellet exits the cannula body.

20 Claims, 18 Drawing Sheets

Related U.S. Application Data which is a continuation-in-part of application No. PCT/US2019/019031, filed on Feb. 21, 2019, and a continuation-in-part of application No. 15/901,837, filed on Feb. 21, 2018, now Pat. No. 10,856,907, and a continuation-in-part of application No. 15/901,821, filed on Feb. 21, 2018, now Pat. No. 11,406,806.

(60) Provisional application No. 63/212,509, filed on Jun. 18, 2021.

(56) References Cited

U.S. PATENT DOCUMENTS

| | | | | |
|---|---|---|---|---|
| 3,630,192 | A * | 12/1971 | Jamshidi | A61B 10/025 |
| | | | | 219/229 |
| 3,921,632 | A | 11/1975 | Bardani | |
| 5,487,739 | A * | 1/1996 | Aebischer | B01J 13/02 |
| | | | | 604/93.01 |
| 5,928,130 | A | 7/1999 | Schmidt | |
| 6,210,315 | B1 | 4/2001 | Andrews et al. | |
| 6,241,734 | B1 | 6/2001 | Scribner et al. | |
| 6,358,195 | B1 | 3/2002 | Green et al. | |
| 6,402,677 | B1 | 6/2002 | Jacobs | |
| 6,450,937 | B1 | 9/2002 | Mercereau et al. | |
| 6,572,525 | B1 | 6/2003 | Yoshizumi | |
| 6,656,106 | B2 | 12/2003 | Schmidt | |
| 6,889,833 | B2 | 5/2005 | Seiler et al. | |
| 7,361,135 | B2 | 4/2008 | Probnik et al. | |
| 7,479,150 | B2 | 1/2009 | Rethy et al. | |
| 2003/0060770 | A1 * | 3/2003 | Wing | A61B 17/3496 |
| | | | | 604/164.02 |
| 2003/0233101 | A1 | 12/2003 | Lubock et al. | |
| 2004/0015133 | A1 | 1/2004 | Karim | |
| 2005/0064046 | A1 | 3/2005 | DiTrolio | |
| 2005/0203565 | A1 | 9/2005 | Rethy et al. | |
| 2006/0063962 | A1 | 3/2006 | Drobnik et al. | |
| 2006/0282042 | A1 | 12/2006 | Walters et al. | |
| 2008/0009792 | A1 | 1/2008 | Henniges et al. | |
| 2009/0131908 | A1 | 5/2009 | McKay | |
| 2012/0253189 | A1 | 10/2012 | Burbank et al. | |
| 2012/0289987 | A1 | 11/2012 | Wilson et al. | |
| 2013/0261596 | A1 | 10/2013 | McKay | |
| 2014/0323808 | A1 | 10/2014 | Evans | |
| 2014/0324090 | A1 | 10/2014 | Kafiluddi et al. | |
| 2016/0175007 | A1 | 6/2016 | Valbuena et al. | |
| 2016/0296739 | A1 * | 10/2016 | Cleveland | A61M 5/31526 |
| 2017/0049972 | A1 | 2/2017 | Persons | |
| 2017/0065805 | A1 | 3/2017 | Tutera | |
| 2018/0085144 | A1 | 3/2018 | McGillicuddy | |

OTHER PUBLICATIONS

Conners, William et al., Outcomes with the "V" Implantation Technique vs. Standard Technique for Testosterone Pellet Therapy, J Sex Med 2011; 8:3465-3470 (Dec. 1, 2011).

*Vitalte Lifesciences Inc.* v. *Bonds Therapeutics LLC* Case No. 4:23-cv-00887 Plaintiff's Answer to Defendant's Counterclaims, Jul. 18, 2023 (5 pages).

*Vitalte Lifesciences Inc.* v. *Bonds Therapeutics LLC* Case No. 4:23-cv-00887-JG Defendant's Answer to Complaint, Jun. 27, 2023 (16 pages).

Chew, S., Basic Laparoscopic Technique and Advanced Endoscopic Suturing: a Practical Guidebook, p. 19 (Jun. 23, 2005).

* cited by examiner

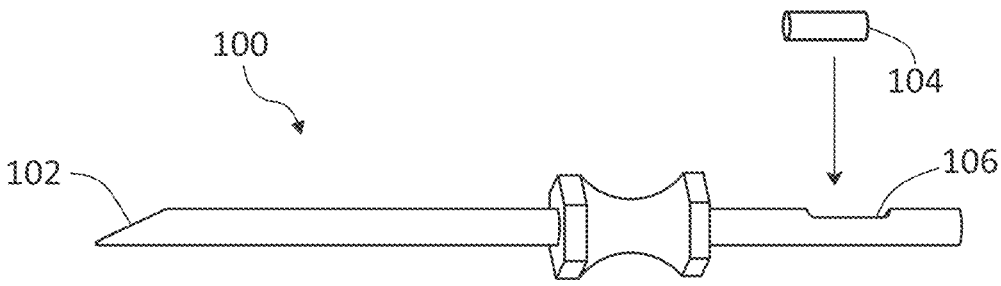
Figure 1A (Prior Art)
Figure 1B (Prior Art)
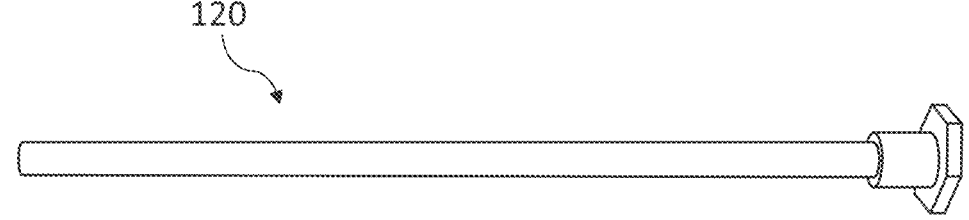
Figure 1C (Prior Art)
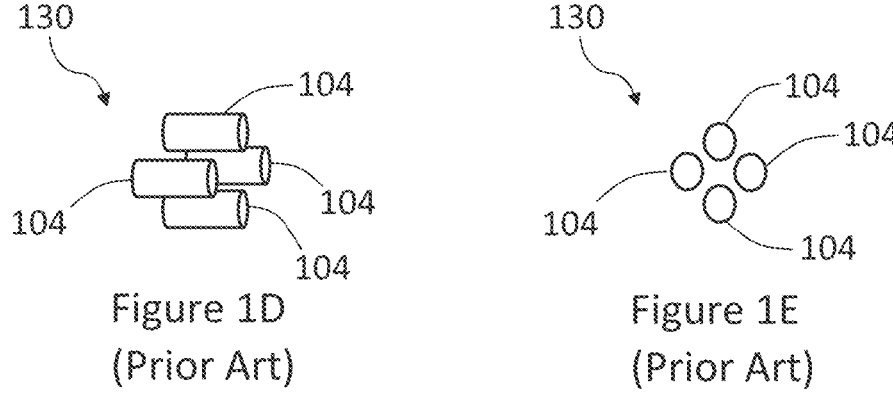
Figure 1D
(Prior Art)
Figure 1E
(Prior Art)

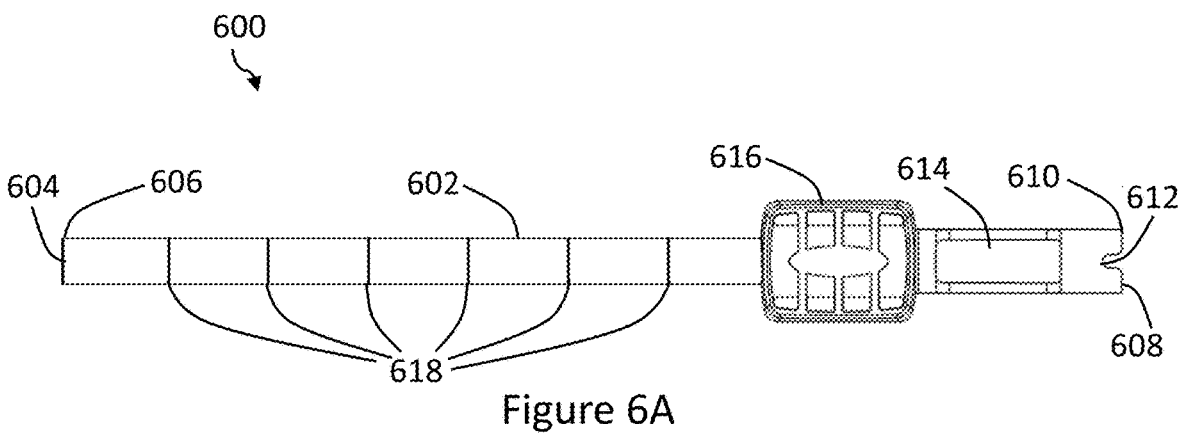
Figure 6A
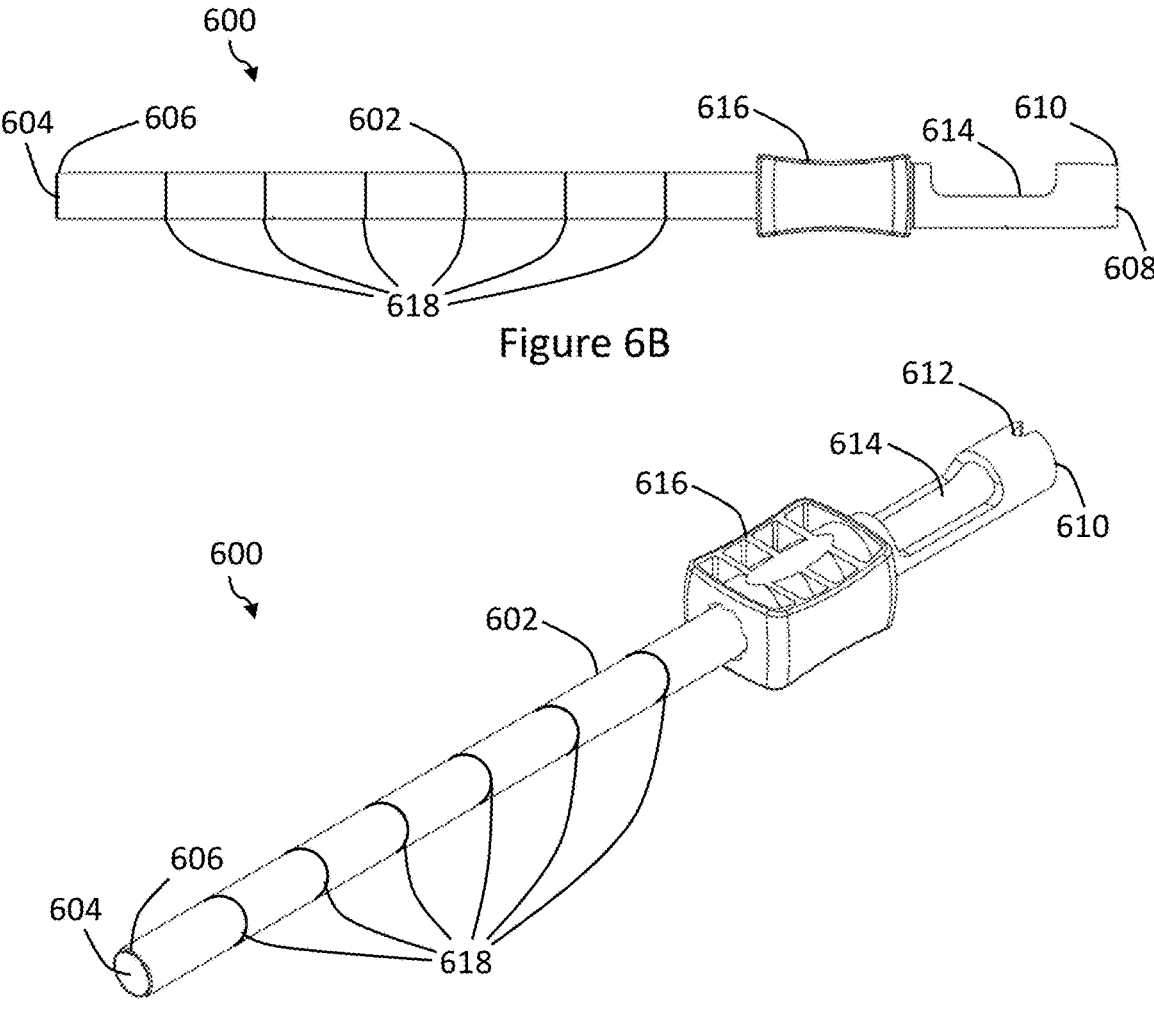
Figure 6B
Figure 6C

Figure 13
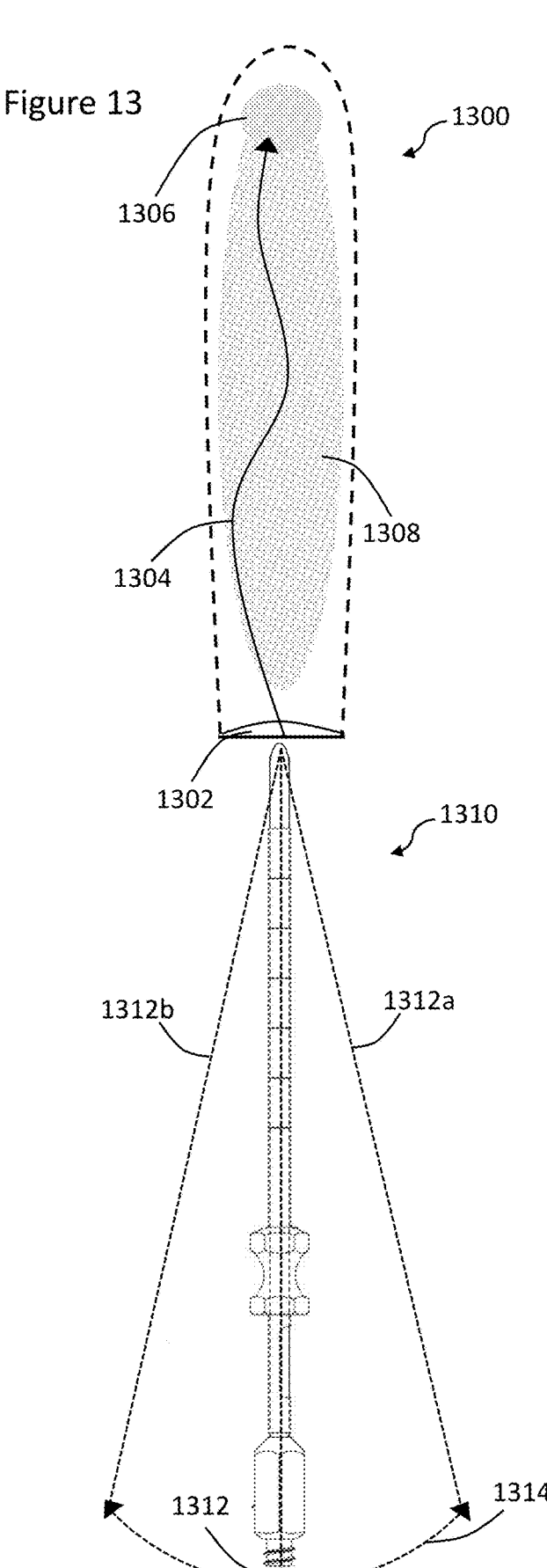
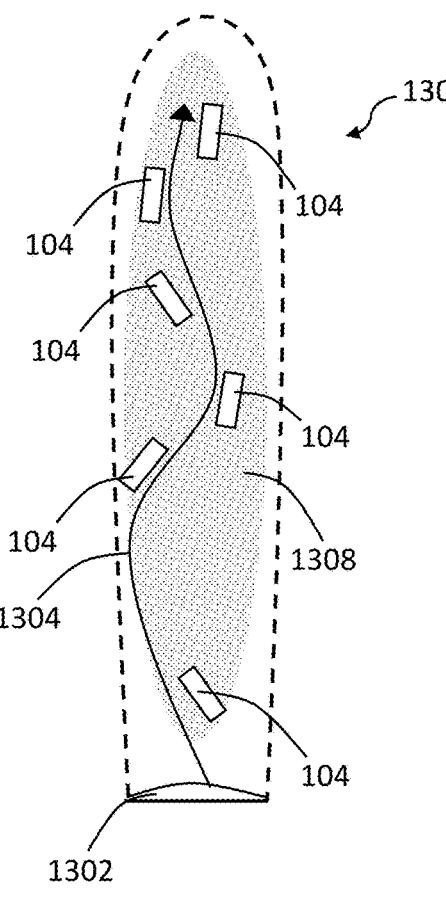
Figure 14

1700

1700

MINIMALLY TRAUMATIC TROCAR METHOD FOR SUBCUTANEOUS MEDICATION DELIVERY

CROSS-REFERENCE

This patent application claims the benefit of provisional patent application No. 63/212,509 filed on Jun. 18, 2021 entitled ATRAUMATIC TROCAR APPARATUS FOR SUBCUTANEOUS MEDICATION DELIVERY;

this patent application is a continuation-in-part of utility patent application Ser. No. 16/997,803 filed on Aug. 19, 2020 entitled ATRAUMATIC SUBCUTANEOUS MEDICATION DELIVERY; (now U.S. Pat. No. 12,042,615);

this patent application is a continuation-in-part of international utility patent application no. PCT/US19/19031 filed on Feb. 21, 2019 entitled ATRAUMATIC SUBCUTANEOUS MEDICATION DELIVERY (published as WO 2019/165131);

this patent application is a continuation-in-part of utility patent application Ser. No. 15/901,837 filed on Feb. 21, 2018 entitled ATRAUMATIC TROCAR MEDICATION DELIVERY METHOD (now U.S. Pat. No. 10,856,907);

this patent application is a continuation-in-part of utility patent application Ser. No. 15/901,821 filed on Feb. 21, 2018 entitled ATRAUMATIC TROCAR APPARATUS, SYSTEM AND KIT (now U.S. Pat. No. 11,406, 806).

All patent applications identified above are hereby incorporated by reference.

FIELD

The present disclosure relates to a minimally traumatic trocar apparatus, system, kit, and method of use. More particularly, the present disclosure relates to a trocar method that includes a cannula that receives an obturator having an anterior rounded tip configured to cause minimal amounts of micro-trauma.

BACKGROUND

Hormone therapies carry significant risks of adverse effects, which can be exacerbated from inconsistent or traumatic delivery as a result of a variety of hormone therapies. Pills may be forgotten by a patient and require relatively frequent pharmacy trips to refill prescriptions. Further, oral delivery can cause gastric distress, destruction of active ingredients (medications), and/or bypass initial metabolism in the liver. Patches may be unsightly, inconvenient, uncomfortable, removed too early, and fail to accommodate individuals requiring higher levels of hormone replacement. Creams may similarly be unsightly and inconvenient, as well as delivering inadequate levels of hormones, requiring repeated application, and allowing for missed applications. Injections require repeated and frequent trips to a doctor's office, and can be painful. Additionally, pill/oral, patch, cream, and injection therapies suffer inconsistent dosage delivery. Dosages of hormones delivered by these techniques tend to spike soon after injection, ingestion, or application, then taper quickly below efficacious medication levels.

Hormone therapies that utilize subcutaneous implants or "pellets" bypass the liver, do not affect clotting factors and do not increase the risk of thrombosis. For example, bioidentical testosterone delivered subcutaneously by pellet implant is cardiac protective, unlike oral, synthetic methyl-testosterone. Subcutaneous pellets have other practical advantages over patches, creams, and injections. Subcutaneous implants release medication consistently for months, freeing patients from frequent trips to the doctor as with injections, and eliminating adherence concerns typical to patient administered medications, such as creams and oral medications. Alternatively, implants or pellet therapy keep hormone levels consistent through the day and avoid rollercoaster-like effects from orally administered, topically administered, or injected hormones. The release of the drug from implanted pellets generally continue for a period of 3 to 6 months, or even up to 12 months, depending on the size and composition of the pellet.

Subcutaneously implanted hormone pellets may be smaller than a grain of rice or approximately the size of a marble and are implanted directly into the subcutaneous tissue, where they provide a slow continuous release of hormone(s) into the bloodstream. Typically, the pellets are implanted in the lower abdomen or buttocks, because of the generally large deposits of fat stored in these areas. The procedure is done in a physician's office with the use of a local anesthetic and a small incision for insertion of a trocar.

Trocar medical devices are commonly used to subcutaneously implant the hormone pellets. Trocar medical devices have been known to, and used by, physicians since at least the 19th century and commonly comprise a hollow tubular cannula and a rod-like obturator that fits snugly within the cannula. A wide variety of trocars exist that vary according to the medical purpose for which they are intended. Trocars are tailored for specific tasks, such as laparoscopic surgery or implant delivery.

With reference now to FIGS. 1A-C, there are shown the components of a prior art trocar apparatus for subcutaneous pellet insertion used in BIOTE® hormone replacement therapy. This prior art embodiment, includes an angled cutting edge formed from the angled orifice 102 of the cannula 100 and the angled tip 112 of the insertion obturator 110. The insertion obturator 110 is machined to fit within the cannula 100 when assembled into a trocar, such that the angled tip 112 of the insertion obturator 110 is flush with the angled orifice 102 of the cannula 100, forming a uniform cutting edge.

As the trocar is inserted into a small surface incision, the angled cutting edge is used to slice through the fatty and connective tissues impeding the passage of the trocar. Once inserted to a desired depth or insertion length, the insertion obturator 110 is removed from the cannula 100 and pellet(s) 104 are loaded into the cannula through a loading slot 106. A blunt delivery obturator 120 is then used in place of the angled insertion obturator to push the pellet(s) 104 through the angled orifice 102 of the cannula 100.

The delivery obturator 120 delivers the pellet(s) to a subcutaneous site. The angled orifice 102 facilitates delivery of multiple pellets 104 in a clumped orientation. With reference now to FIGS. 1D and 1E, a radial clump of pellets 130 is shown. This radial clump 130 is formed by rotating the cannula during extrusion/delivery of the pellets 104 from the angled orifice 102.

The body's primary response to the traumatic cutting insertion of the prior art beveled trocar results in inflamed tissue, lymph fluid, and clotted red blood cells. And the literature from the prior art systems teach that the inflammatory response triggered by traumatic trocar insertion of hormone pellets is critical to adequate hormone absorption.

However, prior art traumatic trocar insertion is painful and results in scarring. Additionally, traumatically inserted pellets may lead to infection or be extruded from the insertion site, which requires replacement with an additional traumatic insertion. Furthermore, the body's inflammatory response to the traumatic insertion causes patients significant pain in the days following insertion. Further still, the cutting and spearing motions used to insert angled or cutting edge trocars cause significant bruising immediately after insertion that lasts for days or weeks, and further cause scarring that may remain for a year or more. Further yet, this inflammatory response increases the healing time of the incision, and increases the probability that one or more pellets may extrude due to external pressures (falling on, sitting on, or bumping the insertion region) or internal pressures (strenuous exercise or muscle contraction).

All of these traumatic trocar insertion concerns are amplified particularly for male testosterone replacement therapy, which requires large gauge trocars and high quantities of implanted pellets. The large trocar gauge and high dosage causes a corresponding amount of pain, scarring, and risk of pellet extrusion.

Therefore, it would be beneficial to provide an apparatus, system, and method of subcutaneous pellet delivery that causes minimal amounts of micro-trauma to the subcutaneous tissue.

SUMMARY

A minimally traumatic trocar method for delivering one or more medication pellet to a subcutaneous insertion site is described. The method begins by receiving a round tipped obturator with a cannula. The cannula includes a tubular cannula body having a smooth anterior surface and a medication slot disposed along the tubular cannula body. The tubular cannula body has an inner diameter of 3 millimeters (mm). The obturator is passed through the tubular cannula body so that the anterior rounded tip of the obturator extends past the smooth anterior surface of the tubular cannula body. The cannula and obturator probe an incision into a subcutaneous tissue along an insertion path within the subcutaneous tissue. The obturator is then removed from the tubular cannula body, and one or more medication pellet is placed in the medication slot of the cannula. The tubular cannula body again receives the obturator, and the anterior rounded tip of the obturator passes the one or more medication pellet through the tubular cannula body so that the obturator pushes the one or more medication pellet through the tubular cannula body and the one or more medication pellet exits the tubular cannula body. By passing the obturator through the tubular cannula body in this manner, the obturator delivers the one or more medication pellet and aligns the one or more medication pellet along the insertion path.

In some embodiments, the method further includes probing along the insertion path in a side-to-side pattern with the cannula and the obturator.

In some embodiments, the insertion path is a linear insertion path. In other embodiments, the insertion path is a non-linear insertion path.

In another embodiment, a method for delivering two or more medication pellets through an incision to a delivery site within a subcutaneous tissue is described. This method begins by receiving an obturator in a cannula. The obturator includes a rounded tip and a tubular obturator body. The cannula includes a tubular cannula body having an anterior end, a posterior end, and a medication slot disposed along the tubular cannula body. The obturator is passed through the tubular cannula body so that the anterior rounded tip of the obturator extends past the anterior end of the tubular cannula body. The cannula and obturator probe the incision into the subcutaneous tissue along a non-linear insertion path within the subcutaneous tissue. The obturator is then removed from the tubular cannula body, and two or more medication pellets are placed in the medication slot of the cannula. The tubular cannula body again receives the obturator, and the anterior rounded tip of the obturator passes the two or more medication pellets through the tubular cannula body so that the obturator pushes the two or more medication pellets through the tubular cannula body and the two or more medication pellets exit the anterior end of the tubular cannula body. By passing the obturator through the tubular cannula body in this manner, the obturator delivers the two or more medication pellets and aligns the two or more medication pellets along the non-linear insertion path.

FIGURES

The presently disclosed subject matter will be more fully understood by reference to the following drawings which are presented for illustrative, not limiting, purposes.

FIG. 1A shows a prior art trocar cannula.

FIG. 1B shows a prior art trocar insertion obturator.

FIG. 1C shows a prior art trocar delivery obturator.

FIG. 1D shows a side view of a prior art radial pellet clump.

FIG. 1E shows a front view of a prior art radial pellet clump.

FIG. 6A shows a top view of a disposable cannula.

FIG. 6B shows a side view of the disposable cannula.

FIG. 6C shows a perspective view of the disposable cannula.

FIG. 13 shows a cut-away view of an illustrative delivery area, assembled minimally traumatic trocar, and side-to-side minimally traumatic subcutaneous probing techniques.

FIG. 14 shows a cut-away view of an illustrative staggered orientation of subcutaneously inserted pellets.

DESCRIPTION

Figures 2A, 2B, 2C:
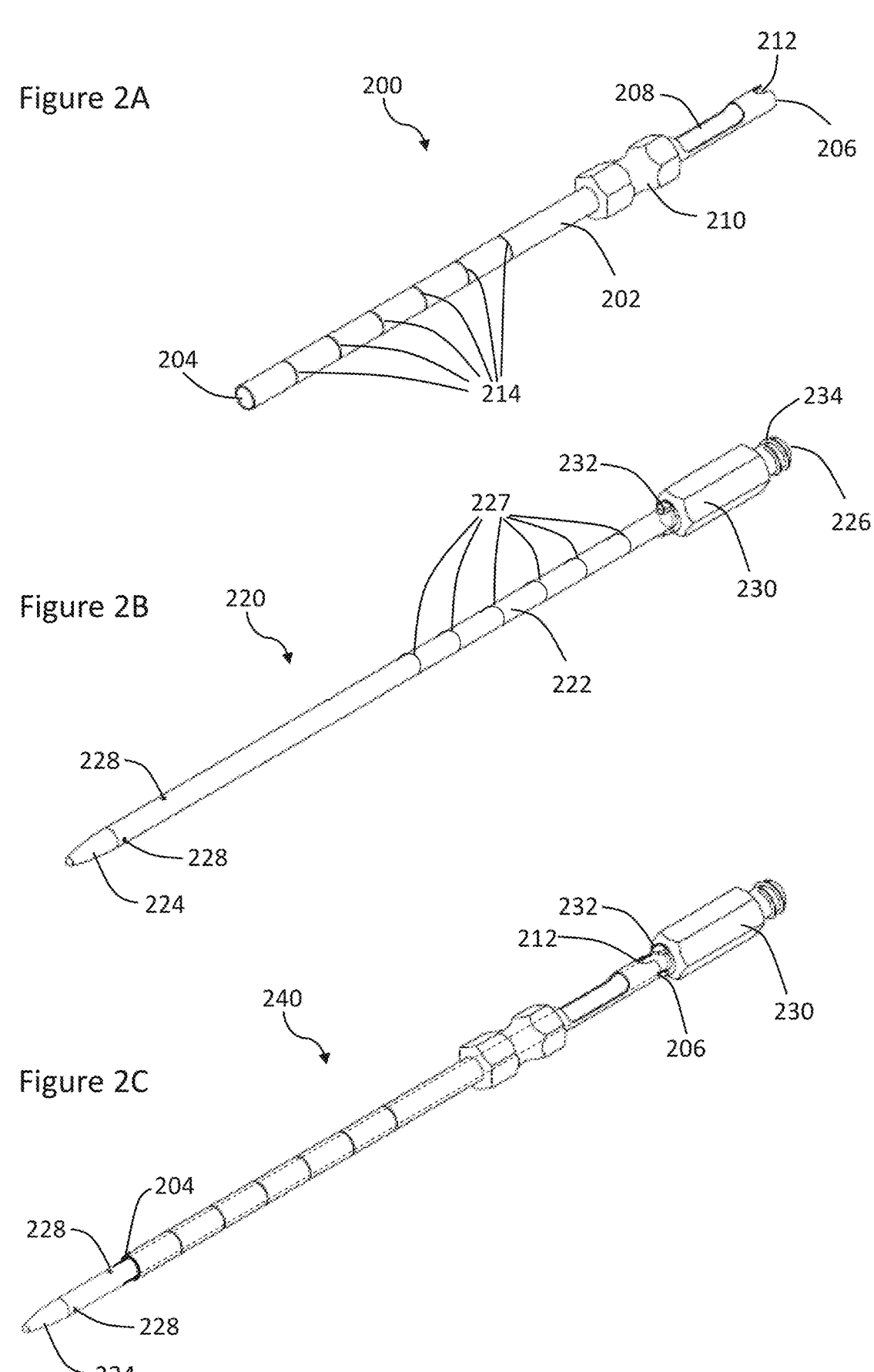
FIG. 2A shows a perspective view of an illustrative embodiment of the cannula as disclosed herein and in accordance with various embodiments.
FIG. 2B shows a perspective view of an obturator.
FIG. 2C shows a perspective view of the obturator placed within the interior passage of the cannula.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and methods described herein may vary as to configuration and as to details. The following detailed description of the illustrative embodiments includes reference to the accompanying drawings, which form a part of this application. The drawings show, by way of illustration, specific embodiments in which the invention may be practiced. It is to be understood that other embodiments may be utilized and structural changes may be made without departing from the scope of the claims.

The apparatus, systems and methods described herein are used to insert an illustrative medication pellet(s) into subcutaneous tissue. Medication pellets may be used for hormone replacement and for other applications that would require a relatively slow and sustained release of one or more medications. Thus, a single pellet may be compounded to contain multiple medications, or different medications may be compounded into individual pellets and delivered together as separate pellets at one insertion site. Pellets inserted with minimal amounts of micro-trauma release medication at consistent and measurable rates for several months up to a year or more.

Inventor hypothesizes that deposits of subcutaneous brown adipose tissue (BAT) have superior blood supplies which beneficially improve medication uptake from subcutaneously inserted medication pellets. Such subcutaneous BAT is known to exist in the anterior abdominal wall and along the vertebral column. As such, the love-handle region, beside the vertebral column (spine), and anterior sides of the abdomen (below and beside the belly/tummy fat) are possible medication pellet delivery locations. These locations are preferred for men due the typically larger doses of medication required as compared to women, and the corresponding larger number and size of medication pellets that must be inserted in order to deliver larger doses of medication. Other possible delivery locations are selected for patient comfort, such as the tensor fascia on the thigh, and the subcutaneous tissue surrounding the gluteus medius or maximus. The love-handle delivery locations are problematic for patients of particular professions, such as police officers and construction workers because they wear utility belts, which may require one of the alternate delivery locations to reduce discomfort and the possibility of extruding delivered medication pellets.

In one therapeutic embodiment, pellets release medication consistently for 6 months before requiring reinsertion of new medication pellets. Upon reaching termination of this 6-month period, the location of the second administration of medication pellets may be rotated. For example, the first administration of medication pellets may be placed above a patient's beltline in their right love-handle region, while the second administration of medication pellets may be placed above the patient's beltline in their left love-handle region. This side-to-side rotation every 6 months allows for complete healing of the first administration site in the patient's right love-handle region prior to any third or re-administration to the patient's right love-handle region, and similarly for re-administration to the patient's left love-handle region.

In general, minimally traumatic implantation requires fewer visits to a doctor's office during a course of treatment compared to injections (lasting for only a matter of days), provides more consistent dosages than patches, creams, and pills, and allows for more complete healing of the insertion sites between administrations. This makes implants or pellets inserted with minimal micro-trauma more efficacious than patches, creams, pills, and traumatically inserted implants or pellets, and more cost effective than injections requiring frequent trips to a doctor's office.

Minimally traumatic subcutaneous medication insertion is also viable for treating pain. Chronic pain management techniques include subdermal surgical insertion of a reservoir and/or pump connected to a catheter that runs directly to the patient's spine to deliver morphine or other anesthetics. This technique may afford relief to a patient for several months between doctor's visits, however the system costs tens of thousands of dollars. In contrast, the minimally traumatic trocar apparatus, system, and method disclosed herein is much more affordable, even allowing for single-use disposable embodiments that deliver relief for several months as well.

As used herein, the term "medication" or "medicinal" includes, but is not limited to, hormones, hormone therapy, pain medication, addiction therapy, and other such drugs.

More specifically, the term "medication" may be used to refer to drugs such as testosterone, estradiol (estrogen), fentanyl, morphine, various opiates, naltrexone, lidocaine and other such drugs. By way of example and not of limitation, "medication" may refer to hormones, opioids, numbing agents, and competitive antagonists in metabolic pathways. For example, "medication" may refer to medicine in pellet form that blocks receptors in the brain, which aid in the treatment of addictive disorders including, but not limited to, alcohol and narcotics.

Minimally traumatic pellet insertion corresponding to the apparatus, systems, and methods disclosed herein can be used for various regimens that include hormone therapy, pain management, and addiction treatment. Further, the apparatus, systems, and methods disclosed herein can be employed in veterinary treatments as well.

With respect to hormone therapy, synthetic, bioidentical, or natural hormones may be used to supplement endogenous hormones naturally produced in the human body. The illustrative apparatus, systems, and methods disclosed herein pertain to the use of medication implants or "pellets." The term "pellet" is used generally to describe both medication pellets and/or hormone implants. Pellets may be prescribed medications or custom compounded therapies for symptoms that stem from hormonal imbalances, to manage hormone levels, to block metabolic pathways involved in the processing of alcohol, opioids, and other addictive drugs, and for pain management.

The pellets described herein may be used for hormone therapies such as menopause and low testosterone. During menopause, individuals experience symptoms including hot flashes, sleep disturbances, and night sweats. Sufferers of low testosterone experience chronic fatigue, loss of muscle mass, increased body fat (especially in the waist area), decreased bone mass, mood changes, lower mental capacity, depression, brain fog, and irritability. Testosterone helps regulate heart function, and plays a part in sperm production, bone health, energy levels, concentration, and muscle mass. Most men experience a natural decline in testosterone as they age, creating a large market for testosterone replacement therapy.

As used herein, the term "hormones" may also refer to synthetic hormones, bioidentical hormones and natural hormones. Synthetic hormones frequently do not have the same structure as endogenous hormones. Synthetic hormones may mimic the effects of endogenous hormones on many biological pathways, but they rarely offer the same effectiveness across all biological pathways. Bioidenticals are exact structural replicas of endogenous hormones and are reported to have much lower incidences of side effects as compared to synthetic hormones. Bioidentical hormones may be derived from plants, such as soy or wild yams. Bioidentical hormones are sometimes defined as molecules identical to a hormone produced by the human body. Natural hormones are those produced in nature by various organisms, and similar to bioidenticals, are identical to a hormone produced by the human body.

A minimally traumatic trocar apparatus, system, and method are described herein. The minimally traumatic trocar apparatus includes a cannula, an obturator, and a hydrodissection microcannula. The cannula includes a tubular cannula body having an anterior cannula end with an anterior cannula opening. The cannula also includes a medication slot disposed along a portion of the tubular cannula body. As described herein, the obturator is received by the cannula and passes through the interior passage of the cannula and exits through the anterior cannula opening. The hydrodissection microcannula includes a tubular microcannula body, an anterior rounded tip, a posterior microcannula opening, and an anterior hydrodissection opening located proximate to the rounded tip. The hydrodissection microcannula is generally of a narrower gauge than both the obturator and the cannula. The hydrodissection microcannula is configured to deliver hydrodissecting fluid through the anterior opening during insertion into subcutaneous tissue. This preliminary delivery of hydrodissecting fluid creates an insertion plane and super-hydrates the tissue surrounding the insertion path. The obturator has a rounded anterior tip and may also include one or more openings near the anterior tip, which are configured to deliver hydrodissecting fluid during insertion of the trocar and before insertion of the medication pellets. However, in embodiments employing the hydrodissection microcannula to prepare a super-hydrated insertion path, the obturator may not include any openings near the anterior tip, and thus not be configured to independently deliver hydrodissecting fluid. In all embodiments, the obturator is further used to deliver the medication pellets to the subcutaneous insertion site.

In some embodiments, the obturator may also be used to deliver medication pellets to the subcutaneous insertion site, eliminating the need for a separate delivery obturator.

The inventor hypothesizes that inserted pellets induce macrophages to aggregate in the injection area through localized angiogenesis. Cytokines can trigger macrophages to transition from innate immunity status to an adaptive immunity status that causes such aggregation. Cytokines are small soluble proteins that mediate the body's inflammatory immune response more generally. Cytokine concentrations triggering inflammatory response ranges widely from 100's of pg/ml to 100's of ng/ml depending upon the various known cytokines. Inventor hypothesizes that serum interleukin-6 is a sensitive, early marker of tissue damage that generally increases concentration at the site of trauma. As such, the greater the surgical trauma, the greater the response of serum interleukin-6 and the greater the peak serum concentration of interleukin-6, which induces C-reactive protein synthesis and inflammation. Localized angiogenesis causes the macrophages to digest the pellet bit by bit from the pellet's outer surface and flush the pellet medication directly into the blood stream over time, resulting in a tissue concentration of the pellet medication corresponding to a desired concentration. Thus, a miniscule level of trauma may improve pellets absorption, while excessive trauma from large bore incising trocars create a much greater inflammatory response that lubricates an unblocked insertion path and hinders absorption of inserted pellets. Often the inflammatory response is so strong and hindering that patients require triamcinolone to suppress the response and enable absorption.

With the atraumatic insertion methods and apparatus disclosed herein, as the pellet size is increased, the medication release period increases, allowing for medication delivery for a period of days up to approximately a year or more. Increasing pellet size also reduces patient cost by reducing the frequency of office visits/operations. Further, increased pellet size allows for the insertion of fewer pellets to achieve the desired amount of medication delivery, i.e. insertion of a single row of medication pellets instead of requiring two rows of medication pellets to achieve the desired amount of medication delivery. Further still, increased pellet size is achieved, indeed only practical, through the minimally traumatic techniques disclosed herein.

The inventor further hypothesizes that a combination of hydrodissection and administration of tranexamic acid reduce patients' soreness, pain, and/or irritation. The hydro-dissection performs several functions: superhydrating and numbing the tissue along the insertion path, as well as preventing the breakdown of clotted blood for 5-6 hours. Superhydration makes tissue along the insertion path softer and more easily shifted during insertion of the minimally traumatic trocar assembly. A later administration of tranexamic acid, such as orally, continues to prevent the breakdown of clotted blood for up to 24 hours after the medication pellet insertion and allows those clots to stabi-lize. Some pain is the result of blood in the insertion space, which irritates pain receptors. A further consequence of reduced amounts of inflammation and blood in the insertion space is improved pellet absorption, healing, and overall patient experience due to reduced pain during and after pellet implantation.

Referring to FIGS. 2A-C there is shown an illustrative minimally traumatic trocar apparatus that includes an illus-trative cannula and an illustrative obturator. More specifi-cally, FIG. 2A shows an illustrative embodiment of a can-nula 200 having a tubular cannula body 202. The tubular cannula body 202 includes an anterior cannula opening 204 located at an anterior end of the cannula 200. The anterior end of the cannula 200 includes a blunt or rounded cylin-drical end, which limits the trauma to surrounding tissue during subcutaneous implant procedures. In one embodi-ment, the cylindrical end of the cannula is blunted by beveling the end. A bevel blunts the cylindrical end of the cannula in this structure, because the beveled edge abuts the outer surface of the obturator tubular body and lies flush or very nearly flush against this outer surface. This blunting may also be achieved with a chamfer, a fillet, rounding to create a rounded shape, or any other method of smoothing the right angle where the outer surface of the tubular body of the cannula meets the cylindrical end of the cannula. In another embodiment, the cylindrical end of the cannula is blunted by burnishing the end. The tubular cannula body 202 further includes a posterior cannula opening 206 located at a posterior end of the cannula 200. The tubular cannula body 202 is hollow, providing a passage through the cannula 200 and connecting the anterior cannula opening 204 to the posterior cannula opening 206. Thus, the tubular cannula body 202 includes an interior passage disposed between the posterior cannula end 206 and the anterior cannula end 204. In various embodiments, the anterior blunt surface sur-rounds the anterior cannula opening.

In the illustrative embodiment, the cannula 200 further includes a slot 208 on a portion of the tubular cannula body 202. The slot 208 is configured or sized to receive a medication pellet and thereby allow the medication access to the interior passage of the cannula 200. The slot 208 may be located proximate to the anterior cannula end. In an alter-native embodiment, the cannula 200 may not include a slot on the tubular cannula body 202, instead receiving medica-tion pellets at the posterior end of the cannula.

By way of example and not of limitation, the illustrative medication pellets described in the embodiments presented herein may include male 200 mg testosterone pellets, male 250 mg testosterone pellets, male 300 testosterone pellets, and male 303 testosterone pellets. The medication pellets have lengths ranging from 10 mm to 15 mm and diameters ranging from 3 mm to 10 mm. In one embodiment, the medication pellets have a length of 13 mm and a diameter of 4 mm. In another embodiment, the medication pellets have a length of 13 mm and a diameter of 5 mm. In another embodiment, the medication pellets have a length of 13 mm and a diameter of 5.6 mm. Female testosterone pellets may include 50 mg to 150 mg, with lengths ranging from 5 mm to 15 mm, and diameters ranging from 2 mm to 5 mm. In an illustrative embodiment, the female testosterone pellet is 87 mg with a 10 mm length and 3 mm diameter. In one embodiment, the cannula may be sized for 5 mm medication pellets for male hormone replacement therapy, e.g. the interior diameter of the cannula is greater than 5 mm. In another embodiment, the cannula may be sized for 4 mm medication pellets for male hormone replacement therapy, e.g. the interior diameter of the cannula is greater than 4 mm and less than 6 mm. In still another embodiment, the cannula may be sized for 3 mm medication pellets for female hormone replacement therapy, e.g. the interior diameter of the cannula is greater than 3 mm and less than 4 mm.

The illustrative cannula 200 may further include a cannula handle 210 fixedly coupled to the tubular cannula body 202. The cannula handle 210 may be permanently affixed to the exterior of the tubular cannula body 202, such as by welding, or removably affixed to the tubular cannula body 202, such as by threading or chemical means. Further, the tubular cannula body 202 and the cannula handle 210 may be machined from a single piece.

By way of example and not of limitation, each of the components of the minimally traumatic trocar apparatus, system and kit may be formed from metallic compounds, metal alloys, plastic materials, polymers or other such materials. The material selected for the minimally traumatic trocar may depend upon whether the minimally traumatic trocar is disposable or non-disposable (reusable). For example, a reusable minimally traumatic trocar apparatus may be constructed from stainless steel so that it can be disinfected in an autoclave. While a disposable minimally traumatic trocar may be composed of a plastic material, such as an extruded plastic, that is intended for single use and is disposal. The extruded plastic may be high grade medical plastic, polystyrene (HIPS), acrylonitrile butadiene styrene (ABS), polypropylene (PP), high, low, or linear low density polyethylene (HDPR, LDPE, LLDPE), rigid polyvinyl chlo-ride (PVC), thermoplastics. Further, the extruded plastic may be non-toxic, free of lead, resistant to chemicals, high temperatures (i.e., sterilization temperatures), high wear, and corrosion resistant.

The illustrative cannula 200 may further include an illus-trative notch 212 located at the posterior end of the tubular cannula body 202. In the illustrative embodiment, the notch 212 is hyperbolic, rectangular, or triangular in shape and configured to interface with a correspondingly shaped tab on an obturator inserted into the interior passage of the cannula 200, as described below. In a further embodiment, the illustrative cannula 200 may include a second notch (not shown) in a second position at the posterior end of the tubular cannula body 202.

The illustrative cannula 200 may further include one or more cannula markings 214 along the tubular cannula body 202. In various embodiments, the cannula markings 214 are visible on the exterior of the tubular cannula body 202. Visibility of the cannula markings 214 may be achieved by scoring, embossing, raising, or coloring. Coloring may include paint, ink, anodizing, or other similarly permanent and visible techniques suitable for use in sterile operations. Where the cannula markings 214 are not scored, embossed, or raised, the cannula markings 214 may be flush with the exterior of the tubular cannula body 202. The cannula markings 214 correspond to a medication length, and serve to aid a doctor or assistant in determining the number of medication pellets or amount of medications administered through the cannula 200. In the illustrative embodiment, the markings 214 are laser etched onto the surface of the cannula 200. In another embodiment, the cannula 200 may include only a single marking 214.

By way of example and not of limitation, the cannula markings 214 may be scored on the surface of an illustrative stainless steel cannula. Alternatively, for a plastic cannula, the cannula markings may be embodied as raised bars, sunk depressions, or flush colored sections on the exterior of the cannula body.

More generally, the illustrative cannula 200 has a total length that may range from 13 centimeters up to 17 centimeters. The total cannula length is measured from the anterior cannula opening 204 to the posterior cannula opening 206. The cannula 200 also has an insertion length that may range from 7 cm to 13 cm. In one embodiment, the cannula 200 has an insertion length of 10 cm. In various embodiments, the tubular cannula body 202 may have an outer diameter ranging from 7 mm down to 3 mm, and an inner diameter ranging from 2 mm to 6 mm. In narrower embodiments, the outer diameter of the tubular cannula body ranges from 6 mm to 7 mm, and the inner diameter ranges from 5 mm to 6 mm. In another narrower embodiment, the outer diameter of the tubular cannula body is 3 mm to 4 mm, and the inner diameter ranges from 2 mm to 3 mm.

In these embodiments, the wall thickness of the tubular cannula body ranges from 2 mm to $\frac{1}{10}$ mm. In the illustrative example, the tubular cannula body is composed of stainless steel and has an outer diameter $5\frac{1}{2}$ mm and an inner diameter of 5 mm; thus, the wall thickness of the tubular cannula body is a $\frac{1}{2}$ mm. Additionally, the illustrative tubular cannula body has a length of between 14 cm and 16.5 cm. In a narrower embodiment, the tubular cannula body length ranges from 15 cm up to 15.6 cm. In an even narrower embodiment, the tubular cannula body length is 15.4 cm.

Referring now to FIG. 2B, there is shown an illustrative embodiment of an obturator 220 having a tubular obturator body 222, an anterior rounded tip 224, a posterior obturator opening 226, and one or more medication delivery markings 227 along the tubular body of the obturator 222. The tubular obturator body 222 is hollow from the anterior rounded tip 224 to and through the posterior obturator opening 226. By way of example and not of limitation, the illustrative obturator has a length of between 7 inches and 8 inches, an outer diameter of between 6 mm and 2.8 mm, an inner diameter of between 5.7 mm and 2.5 mm, and a wall thickness of between 0.1 mm and 0.5 mm. In a narrower embodiment, the obturator has a length of between 7.25 inches and 7.75 inches, an outer diameter of between 6 mm and 5.5 mm, and an inner diameter of between 5.7 mm and 5.2 mm. In another narrower embodiment, the obturator has a length of between 7 inches and 7.5 inches, an outer diameter of between 4.1 mm and 3.6 mm, and an inner diameter of between 3.8 mm and 3.3 mm. In an even narrower embodiment, the obturator length is 7.5 inches, the outer diameter is 4.8 mm, and the inner diameter is 4.3 mm; thus, the wall thickness for the obturator is $\frac{1}{2}$ mm.

Thus, in a broad embodiment, the tolerance between the outer diameter of the obturator and the inner diameter of the cannula is 0.05 inches. In a narrower embodiment, the tolerance between the outer diameter of the obturator and the inner diameter of the cannula is 0.01 inches. In an even narrower embodiment, the tolerance between the outer diameter of the obturator and the inner diameter of the cannula is 0.001 inches. And in a still narrower embodiment, the tolerance between the outer diameter of the obturator and the inner diameter of the cannula is 0.0005 inches.

The anterior rounded tip 224 comprises a blunt surface. The blunt surface formed by the anterior cannula end and anterior blunt tip of the obturator 240 may be a continuous smooth surface or a semi-continuous smooth surface. The anterior rounded tip 224 may be a rounded cone, a flat-topped cone, a spherical cap, or a semi-spherical cap. A similarly continuously smooth or semi-continuously smooth blunt surface or edge may be formed by the blunt anterior cannula end and the anterior blunt tip of the obturator. In the illustrative embodiment, the blunt surface includes rounded or beveled edges of the anterior end of the cannula. The combination of the anterior cannula end and the blunt anterior tip 224 of the obturator 220 is blunt or rounded to reduce or prevent instances of tissue tearing during the subcutaneous pellet insertion procedure.

The medication delivery markings 227 along the tubular body of the obturator 222 aid in delivery of medication pellets from the cannula 200 to a delivery site. In various embodiments, the delivery markings 227 are visible on the exterior of the tubular body of the obturator 222. Visibility of the delivery markings 227 may be achieved by scoring, embossing, or coloring. Coloring may include paint, ink, anodizing, or any suitable flush marking technique. Where the delivery markings 227 are not recessed or scored, the delivery markings 227 may be flush with the exterior of the tubular body of the obturator 222. The delivery markings 227 correspond to a medication length, and serve to aid a surgeon, nurse, physician's assistant, or other medical professional in determining the number of medications or amount of medications administered through the cannula 200 with the obturator 220. In one embodiment, the delivery markings 227 correspond to a medication length of $\frac{1}{2}$ inch. In a further embodiment, the delivery markings correspond to cannula markings 214 that are also spaced $\frac{1}{2}$ inch apart from one another. In another embodiment, the delivery markings 227 correspond to a medication length of 1 cm. In this other embodiment, the delivery markings correspond to cannula markings 214 that are also spaced 1 cm apart from one another. However, in alternative embodiments, the delivery markings 227 and cannula markings 214 correspond to medication lengths ranging from 2.5 mm to 18 mm.

The illustrative obturator 220 further includes one or more openings 228 located along the tubular obturator body 222. The openings 228 form a passage from the exterior of the tubular obturator body 222 to the interior of the tubular obturator body 222. In the illustrative embodiment, the openings 228 are arranged on the obturator 220 from the anterior rounded tip 224 along the entire length of the obturator body 222 in a spiral orientation. In other embodiments, the openings 228 may be located on and about the anterior rounded tip 224. By way of example and not of limitation, the openings are approximately 1 mm in diameter. In various embodiments, the openings can range in diameter from $\frac{1}{4}$ mm up to 2.5 mm.

The openings 228 enable the obturator to more easily separate the subcutaneous tissue, adipose tissue, blood vessels, and nerves through hydrodissection. Hydrodissection is a well-known technique in ophthalmologic surgery and general surgery where a fluid, such as saline is injected into a target tissue to create a previously non-existent surgical plane. In ophthalmologic surgery hydrodissection is used to create space within the lens, thereby improving a surgeon's ability to perform maneuvers during extracapsular or phacoemulsification surgeries. In general surgery, hydrodissection is used in conjunction with ultrasonic guidance to treat peripheral nerve entrapments by releasing the nerves' adhesions from neighboring structures. When releasing entrapped nerves with hydrodissection the fluid used may be platelet-rich plasma ("PRP") or a 5% dextrose solution ("D5W"). In the illustrative embodiments disclosed herein the hydrodissecting fluid delivered through the openings 228 includes PRP, D5W, saline, anesthetic, a numbing solution, lidocaine, epinephrine, antifibrinolytic compounds (i.e., tranexamic acid), or any combination thereof. In other embodiments, the hydrodissecting fluid includes 0.1 to 2 parts tranexamic acid, 8 to 9.9 parts 1% lidocaine solution, and $\frac{1}{1,000,000}$ to $\frac{1}{1,000}$ parts epinephrine. In a narrower embodiment, the hydrodissecting fluid includes 1 mL tranexamic acid, 9 mL 1% lidocaine solution, and $\frac{1}{100,000}$ epinephrine (i.e., 1 g epinephrine in 100,000 mL hydrodissecting solution).

Hydrodissection during the minimally traumatic subcutaneous pellet delivery systems and methods disclosed herein allows the obturator to separate the subcutaneous tissue, adipose tissue, blood vessels, and nerves prior to arrival of the anterior blunt tip of the obturator. This preparation of the tissue into which the minimally traumatic trocar is inserted softens, hydrates, and/or superhydrates the tissue, easing and improving the maneuverability of the minimally traumatic trocar within the tissue. Additionally, where the hydrodissection fluid includes lidocaine or other numbing agents, the hydrodissection fluid operates to numb the tissue and/or block nerves along the insertion path, which reduces a patient's pain level during and immediately after medication pellet insertion with only minimal amounts of micro-traumatic. Where the hydrodissection fluid includes epinephrine, the hydrodissection fluid operates to constricts the blood vessels and reduce bleeding from any tissue punctured, torn, or irritated along the insertion path. Where the hydrodissection fluid includes an antifibrinolytic compound, such as tranexamic acid, the hydrodissection fluid operates to slow the breakdown of any blood clots that form along the insertion path, which reduces or prevents prolonged bleeding from minimally traumatic medication pellet insertion.

The illustrative obturator 220 may further include an obturator handle 230 fixedly coupled to the tubular obturator body 222. The obturator handle 230 may be integral to the tubular obturator body 222; permanently affixed to the exterior of the tubular obturator body 222, such as by welding, glue, or epoxy; or removably affixed to the tubular obturator body 222, such as by threading or chemical means.

Further still, the illustrative obturator 220 may include a tab 232 configured to interface with the notch 212 on the posterior end of the cannula 200. The tab 232 may be located adjacent to the obturator handle 230 and may be located on the exterior surface of the obturator tubular body 222. The tab 232 may be raised above the exterior surface of the obturator tubular body 222. The tab 232 is fixedly coupled to one of the obturator handle 230 and the obturator tubular body 222. In various embodiments, the tab 232 and the obturator handle 230 are formed from a single machined piece. In some embodiments, the obturator 220 includes a second tab 233 located at a second position about the exterior surface of the obturator tubular body 222.

In a broad embodiment, the tolerance between the notch 212 and the tab 232 is 0.05 inches. In a narrower embodiment, the tolerance between the notch 212 and the tab 232 is 0.01 inches. In an even narrower embodiment, the tolerance between the notch 212 and the tab 232 is 0.001 inches. And in a still narrower embodiment, the tolerance between the notch 212 and the tab 232 is 0.0005 inches.

The insertion obturator 220 may further include a threaded posterior end 234. The threaded posterior end 234 may be configured to receive a medication, numbing solution, anesthetic, and/or hydrodissecting fluid through a tubing from a syringe pump or other reservoir. By way of example and not of limitation, the threaded posterior end 234 includes a luer lock receptor, which is configured to interface with tubing that delivers a numbing solution, anesthetic, and/or hydrodissecting fluid. The numbing solution may include saline, lidocaine, and/or epinephrine. The tubing can be plastic, rubber, flexible, or rigid. In some embodiments, the threaded posterior end 234 surrounds the posterior obturator opening 226.

More generally, the illustrative obturator 220 has a total length that may range from eighteen (18) centimeters up to twenty-two (22) centimeters, and an insertion length that may range from 15 cm up to 19 cm. The total obturator length is measured from the anterior point of the anterior rounded tip 224 to the posterior obturator opening 226. The insertion length is measured from the anterior point of the anterior rounded tip 224 to the anterior surface of the obturator handle 230. In one embodiment, the total obturator length is 19 cm and the insertion length is 16 cm.

In various embodiments, the obturator 220 is a single stainless steel or titanium piece, with no weak joints susceptible to failure. Thus, no element of the obturator 220 is likely to break or separate from a main body of the obturator and remain inside a patient's dermis or other cavity.

Referring now to FIG. 2C, there is shown the illustrative obturator 220 inserted into the interior passage of the illustrative cannula 200 to form a non-disposable minimally traumatic trocar 240, in which the portion of the obturator tubular body 222 within the interior passage of the cannula 200 is shown with dotted lines.

In the illustrative embodiment, the obturator 220 is long enough in comparison to the cannula 200, that the rounded tip 224 and at least one opening 228 protrude beyond the anterior end of the cannula 200 and through the anterior cannula opening 204 when the obturator 220 is inserted into the cannula 200 so that the tab 232 interfaces with the notch 212. In this illustrative embodiment, the rounded tip 224 may protrude up to 1 cm beyond the anterior end of the cannula 200 so that the rounded tip 224 separates tissue up to approximately 1 cm distal or in front of the anterior end of the cannula 200 with minimal micro-trauma upon insertion of the assembled trocar through an incision site to an insertion site. This additional length of the obturator 220 modifies tissue so that a later inserted medication pellet can be extruded further into the tissue, for example by tunneling the medication pellet through the tissue displaced by the additional length of the obturator 220 extending beyond the anterior end of the cannula 200.

In another embodiment, the obturator 220 is long enough in comparison to the cannula 200, that only the anterior rounded tip 224 protrudes beyond the anterior end of the cannula 200 and through the anterior cannula opening 204 when the obturator 220 is inserted into the cannula 200 so that the tab 232 interfaces with the notch 212.

In other embodiments, the obturator 220 is long enough in comparison to the cannula 200, that the rounded tip 224 and at least one opening 228 protrude beyond the anterior end of the cannula 200 and through the anterior cannula opening 204 when the obturator 220 is inserted into the cannula 200 so that the obturator handle 230 abuts the posterior cannula end.

Figures 3A, 3B:
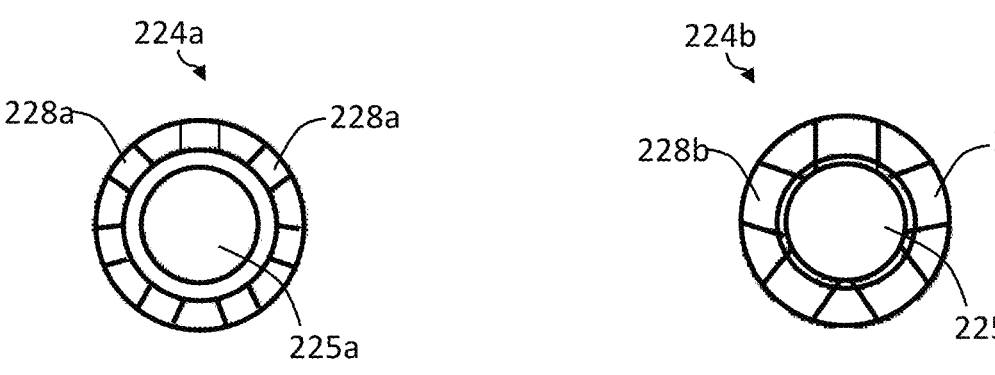
FIG. 3A shows an end-on view of an illustrative obturator rounded tip with seven (7) openings.
FIG. 3B shows an end-on view of an illustrative obturator rounded tip with five (5) openings.

Referring now to FIG. 3A, there is shown an illustrative obturator anterior rounded tip 224a having seven (7) openings 228a. The illustrative openings 228a may be proximate to the anterior point of the rounded tip 225a and arrayed in a spiral pattern along the tubular body of the obturator 222, such that a second opening is 1 cm further from the anterior point of the rounded tip 225a than a first opening and radially separated from the first opening by an angle of 30 degrees. This separation may be greater, such as 2 cm and 60 degrees, or any combination of these linear and radial separations. Generally, the spiral pattern is achieved by continuation of the same separation from the second opening to a third opening as that from the first opening to the second opening. The openings 228a pass through the outer surface of the obturator to the interior. In an alternative embodiment, the openings 228a are arrayed in a circular pattern about the anterior rounded tip 224a, such that the openings 228a are in a plane perpendicular to the length of the obturator 220. In this alternative embodiment, the openings 228a are located in proximity to the anterior point of the rounded tip 225a, such as within 2 cm of the anterior point of the rounded tip 225a. In a modification of this alternative embodiment, the openings 228a are arrayed in a plane perpendicular to the length of the obturator 220, and located within 1 cm of the anterior point of the rounded tip 225a. In these alternative embodiments, the openings 228a are arrayed such that none of the openings 228a are situated along the tubular obturator body 222 and all of the openings 228a are equally distal, proximate, or distant from the anterior point of the rounded tip 225a.

Referring now to FIG. 3B, there is shown another illustrative obturator anterior rounded tip 224b having five (5) openings 228b. The illustrative openings 228b may be proximate to the anterior point of the rounded tip 225b and are arrayed in a spiral pattern along the tubular body of the obturator 222. The openings 228b pass through the outer surface of the obturator to the interior. In an alternative embodiment, the openings 228b are arrayed in a circular pattern about the anterior rounded tip 224b, such that the openings 228b are in a plane perpendicular to the length of the obturator 220. In this alternative embodiment, the openings 228b are located in proximity to the anterior point of the rounded tip 225b, such as within 2 cm of the anterior point of the rounded tip 225b. In a modification of this alternative embodiment, the openings 228b are arrayed in a plane perpendicular to the length of the obturator 220, and located within 1 cm of the anterior point of the rounded tip 225b. In these alternative embodiments, the openings 228b are arrayed such that none of the openings 228b are situated along the tubular obturator body 222 and all of the openings 228b are equally distal, proximate, or distant from the anterior point of the rounded tip 225b.

Figure 3C:
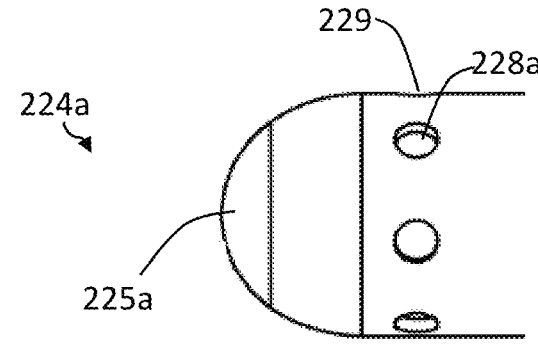
FIG. 3C shows a perspective view of the obturator rounded tip with seven (7) openings proximate to the end of the rounded tip.

Referring now to FIG. 3C, there is shown a side view of the illustrative obturator anterior rounded tip 224a and some of its seven (7) openings 228a arrayed in a plane perpendicular to the length of the obturator. Three (3) of the openings 228a are in view, one (1) opening 229 is partially in view, and the remaining three (3) openings are not visible on the reverse side of the obturator. In this illustrative embodiment, the openings 228 are set back from the terminus of the tip 224 and entirely located on the tubular obturator body instead of any rounded portion of the tip 224.

Figure 3D:
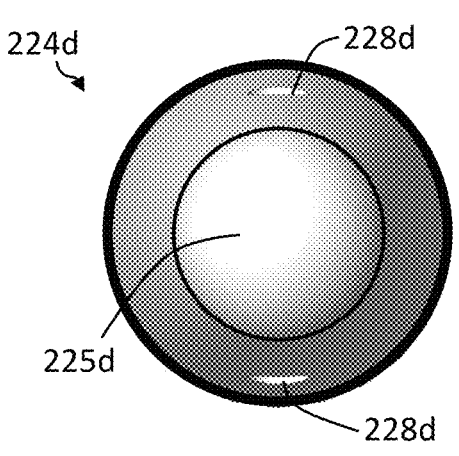
FIG. 3D shows an end-on view of an illustrative obturator rounded tip with two (2) openings.

With reference now to FIG. 3D, there is shown another illustrative obturator anterior rounded tip 224d having two (2) openings 228d. The illustrative openings 228d may be proximate to the anterior point of the rounded tip 225d and are arrayed in a plane perpendicular to the length of the obturator 220. The openings 228d are located in proximity to the anterior point of the rounded tip 225d, such as within 2 cm of the anterior point of the rounded tip 225d. In another embodiment, the openings 228d are arrayed in a plane perpendicular to the length of the obturator 220, and located within 1 cm of the anterior point of the rounded tip 225d. In these embodiments, the openings 228d are arrayed such that none of the openings 228d are situated along the tubular obturator body 222 and all of the openings 228d are equally distal, proximate, or distant from the anterior point of the rounded tip 225d.

Figure 3E:
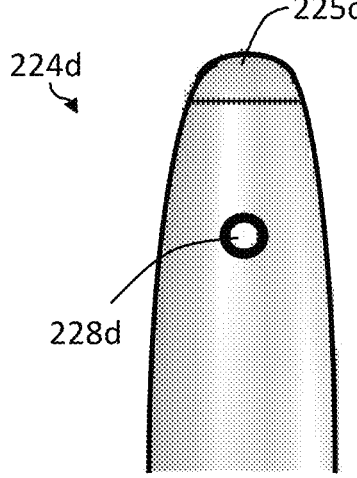
FIG. 3E shows a perspective view of the obturator rounded tip with two (2) openings proximate to the end of the rounded tip.

Referring now to FIG. 3E, there is shown a side view of the illustrative obturator anterior rounded tip 224d and one (1) of its two (2) openings 228d arrayed in a plane perpendicular to the length of the obturator. The one opening not shown is not visible on the reverse side of the anterior rounded tip 224d. In this illustrative embodiment, the openings 228 are set back from the terminus of the tip 224 and located on rounded portion of the tip 224, instead of being partially or entirely located on the tubular obturator body.

As the number of openings proximate to the obturator anterior rounded tip 224 increase, the strength and durability of the tip 224 decreases. Therefore, certain embodiments may include fewer openings, such as one, two, three, or four openings. The reduced number of openings increases the structural integrity of the obturator 220, and in particular the anterior rounded tip 224 of the obturator 220. A further attribute of reducing the number of openings is an increased pressure of numbing solution or anesthetic delivered through the opening(s). As described below, increasing the delivery pressure of the numbing solution may improve hydrodissection, which has the advantageous effect of softening tissues and creating a surgical plane or fluid channel into which pellets are delivered.

Figure 4A:
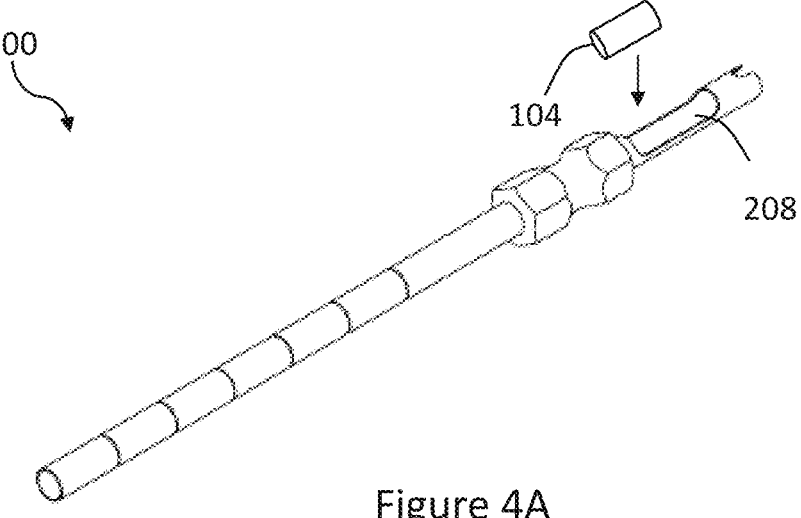
FIG. 4A shows a perspective view of the cannula receiving a medication pellet.
Figure 4B:
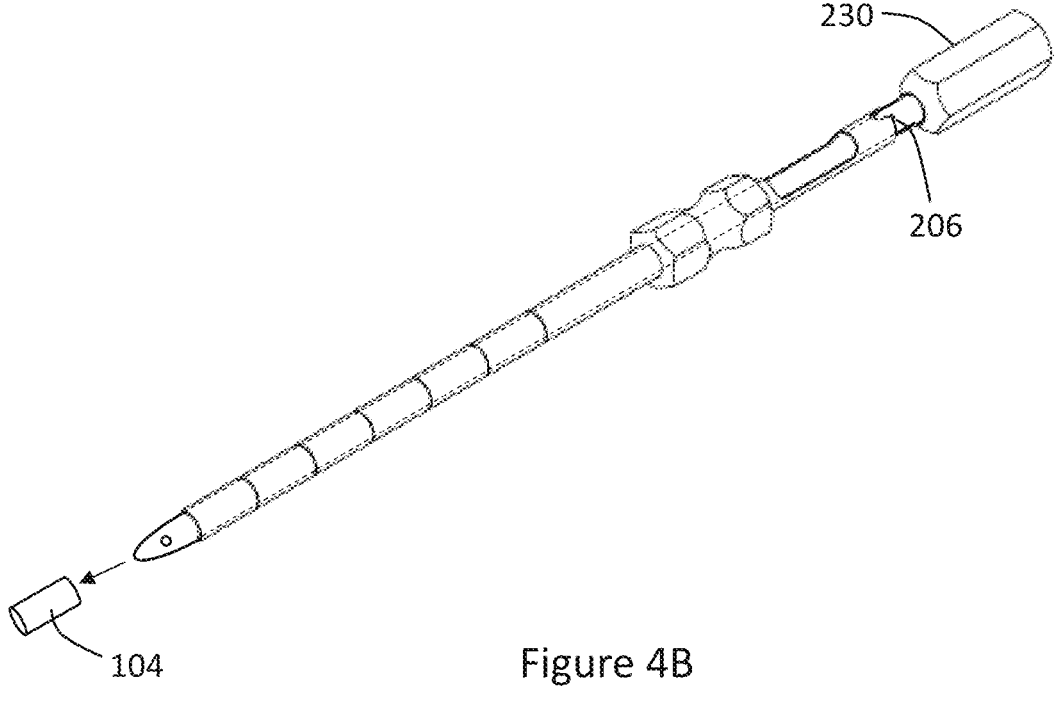
FIG. 4B shows a perspective view of the obturator placed within the interior passage of the cannula so that the obturator extrudes a medication pellet.

With reference now to FIG. 4A, there is shown an illustrative cannula 200 receiving a medication pellet 104 at the medication slot 208. The received medication pellet 104 resides within the interior passage of the cannula 200. By way of example and not of limitation, the medication slot 208 ranges in length from 0.6 inches down to 0.35 inches. In an illustrative embodiment, the medication slot 208 is 14 mm long and is configured to receive a ½ inch (13 mm) long medication pellet.

Referring now to FIG. 4C, there is shown the illustrative obturator 220 inserted into the interior passage of the illustrative cannula 200 such that at least one medication pellet 104 passes through the anterior opening of the cannula 200. The portion of the obturator tubular body 222 within the interior passage of the cannula 200 is shown with dotted lines. The obturator 220 is long enough in comparison to the cannula 200 that the anterior blunt tip 224 is of sufficient length to pass the medication pellet(s) through the cannula.

For example, the obturator 220 may extend up to one (1) centimeter beyond the anterior end of the cannula 200. In this embodiment, the obturator is long enough to push one or more pellets 104 to and through the anterior cannula opening 204.

In another embodiment, the obturator 220 is only long enough in comparison to the cannula 200 that the anterior blunt tip 224 is flush with the anterior end of the cannula 200 and the anterior cannula opening 204 when the obturator 220 is inserted into the cannula 200 to a maximum allowable extent. The maximum allowable extent is the point at which the obturator handle 230 abuts the posterior cannula opening 206 and the posterior end of the cannula 200.

The minimally traumatic trocar apparatus described above may be embodied in a kit that includes the cannula 200, the obturator 220, a hydrodissection microcannula, and an outer package that houses the cannula, obturator, and hydrodissection microcannula. By way of example and not of limitation, the illustrative minimally traumatic trocar kit may also include a scalpel, scissors, forceps, bandages, a sterile field drape, gauze, antiseptic ointments, a wound closure component, and other such materials that may be used during the medical procedure. The scalpel may include the illustrative punch scalpel described below. In another embodiment, the kit includes a disposable trocar as described below.

Figure 5A:
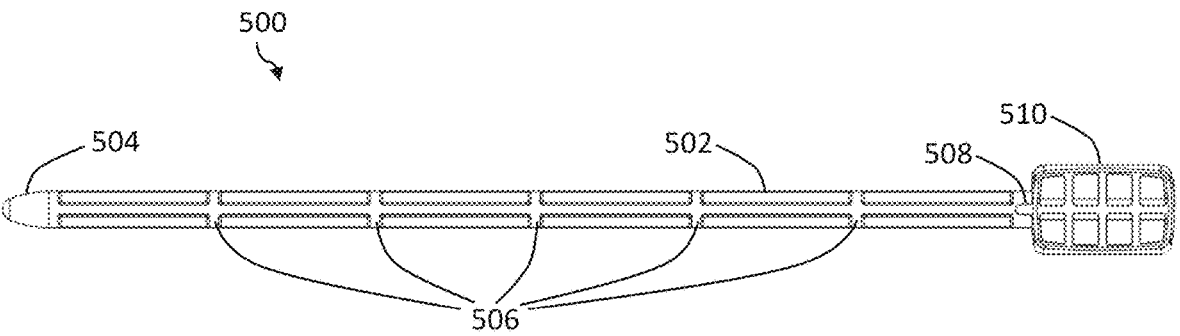
FIG. 5A shows a top view of a disposable obturator.

Referring now to FIG. 5A, there is shown a top view of an illustrative disposable obturator 500 having a tubular body 502, an anterior rounded tip 504, and one or more medication delivery markings 506 along the tubular body of the obturator 502. The illustrative disposable obturator 500 also includes one or more tabs 508 and a textured handle 510. In the illustrative embodiment, the tubular body 502 is of a solid construction with structural ribs representing or performing the secondary function of the medication delivery markings 506. This solid construction prevents the disposable obturator 500 from being hollow or delivering hydrodissection fluid. The illustrative disposable obturator may be composed of a plastic material, such as an extruded plastic, that is intended for single use and is disposal. The extruded plastic may be high grade medical plastic, polystyrene (HIPS), acrylonitrile butadiene styrene (ABS), polypropylene (PP), high, low, or linear low density polyethylene (HDPR, LDPE, LLDPE), rigid polyvinyl chloride (PVC), thermoplastics. Further, the extruded plastic may be non-toxic, free of lead, resistant to chemicals, high temperatures (i.e., sterilization temperatures), high wear, and corrosion resistant.

By way of example and not of limitation, the illustrative disposable obturator has a length from the anterior tip 504 to the textured handle 510 of between 4 inches and 7 inches and an outer diameter of between 6 mm and 3 mm. In a narrower embodiment, the obturator has a length of between 4½ and 5 inches and an outer diameter of between 3.3 mm and 3.7 mm. In one embodiment, the obturator length is 4.8 inches and the outer diameter is 3.5 mm. In another narrow embodiment, the obturator has a length of between 6 and 6.7 inches and an outer diameter of between 4½ mm and 6 mm. In one embodiment, the obturator length is 6.3 inches and the outer diameter is 4.9 mm. In another embodiment, the obturator length is 6.4 inches and the outer diameter is 5.6 mm.

The anterior rounded tip 504 may have substantially the same shape as the non-disposable anterior rounded tip 224 described in FIGS. 2B, 2C, 3A, 3B, 3C, 3D, 3E. Thus, the anterior rounded tip 224 comprises a blunt surface that may be a continuous smooth surface or a semi-continuous smooth surface.

The textured handle 510 has a honeycombed structure that simultaneously reduces the amount of material required to form the handle and provides texture for gripping the handle. The solid structure of the obturator prevents delivery of hydrodissecting fluid through the obturator during insertion of the assembled disposable trocar into the subcutaneous tissue. However, this solid construction also obviates the need of a luer lock receptor on the posterior portion of the obturator handle, and provides the user with a more ergonomic grip that is easier for the user to manipulate during subcutaneous insertion.

Figure 5B:
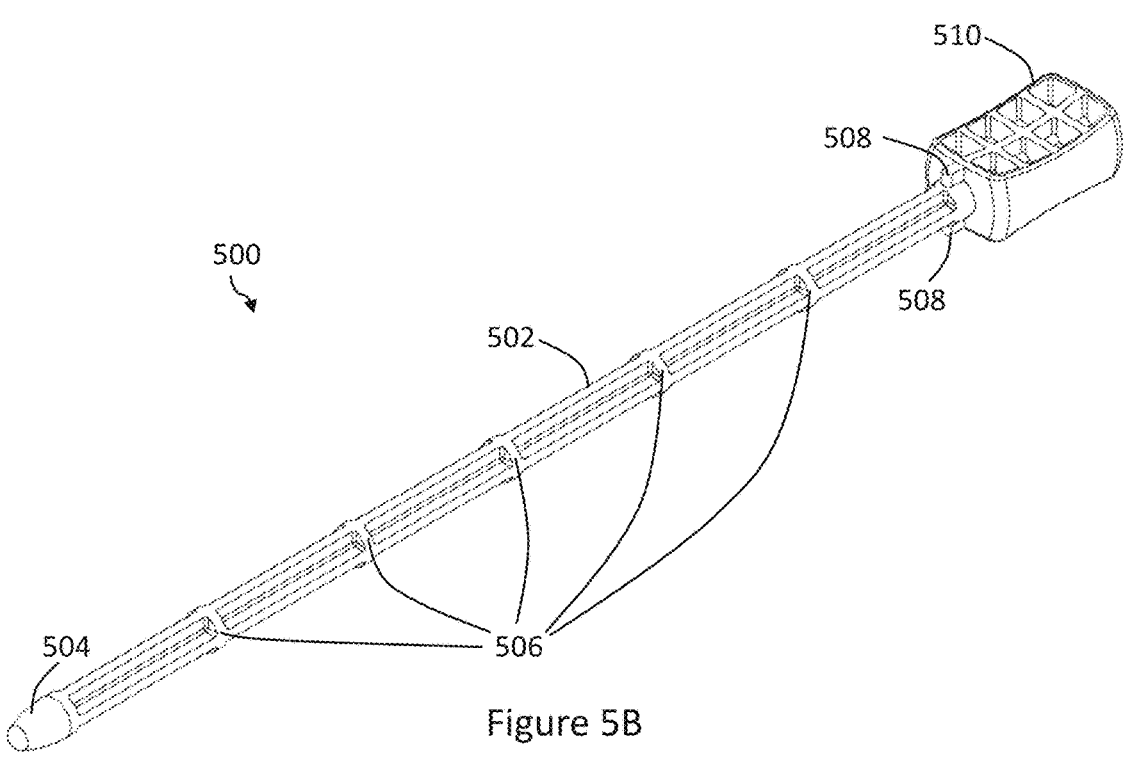
FIG. 5B shows a perspective view of the disposable obturator.

With reference now to FIG. 5B, there is shown a perspective view of the illustrative disposable obturator 500. In this view, a depth or relief of the structural ribs or medication markings 506 can be seen. This depth or relief represents negative space formed as a result of the structure of the disposable obturator 500. In the illustrative embodiment, the tubular body 502 of the disposable obturator is formed from two linear bars running lengthwise and oriented perpendicular to one another. These linear bars are supported by the medication marking ribs 506, which are oriented orthogonal to the two linear bars, i.e. perpendicular to each linear bar.

This view also shows the height and orientation of two tabs 508 adjacent to the textured handle 510. These tabs 508 are oriented with a long axis running parallel to the length of the disposable obturator tubular body 502. Further, the tabs 508 are located radially about an outer surface of the disposable obturator tubular body 502, such that the tabs are radially separated from one another by 180°. In other embodiments, fewer or greater than two tabs 508 are included on the disposable obturator. The orientation of the tabs 508 may be such that they are radially equidistant about the surface of the disposable obturator tubular body 502 from each other, i.e. three tabs are separated by 120° each, four tabs are separated by 90° each, and so on. In other embodiments, the tabs 508 may be oriented radially non-equidistant from one another about the surface of the disposable obturator tubular body 502.

This view further shows the hollow recesses forming the honeycombed structure of the textured handle 510. These hollow recesses may extend fully through the textured handle 510. In another embodiment, these hollow recesses may not extend fully through the textured handle 510, but instead stop at a solid division within the textured handle 510 that separates a top side of the textured handle 510 from a bottom side of the textured handle 510. In some embodiments, the texture arises from cavities or depressions and ridges on the surface of the textured handle 510.

Referring now to FIG. 6A, there is shown an illustrative disposable cannula 600, having a tubular cannula body 602. The tubular cannula body 602 includes an anterior cannula opening 604 located at an anterior end 606 of the disposable cannula 600. The anterior end 606 of the disposable cannula 600 includes a blunt or rounded cylindrical end, which limits the trauma to surrounding tissue during subcutaneous implant procedure. In one embodiment, the cylindrical end of the cannula is blunted by beveling the end. The bevel blunts the cylindrical end of the cannula in this structure, because the beveled edge abuts the outer surface of the obturator tubular body and lies flush or very nearly flush against this outer surface. This blunting may also be achieved with a chamfer, a fillet, rounding to create a rounded shape, or any other method of smoothing the right angle where the outer surface of the tubular body of the cannula meets the cylindrical end of the cannula. The tubular cannula body 602 further includes a posterior cannula opening 608 located at a posterior end 610 of the disposable cannula 600. The tubular cannula body 602 is hollow, providing a passage through the disposable cannula 600 and connecting the anterior cannula opening 604 to the posterior cannula opening 608. Thus, the tubular cannula body 602 includes an interior passage disposed between the posterior cannula end 610 and the anterior cannula end 606.

In the illustrative embodiment, the posterior end 610 of the disposable cannula 600 includes one or more notches 612 configured to interface or interlock with one or more tabs 508 of the disposable obturator 500 upon full insertion of the disposable obturator 500 into the interior passage of the disposable cannula 600. In illustrative embodiment, the one or more notches 612 are located at the posterior end 610 of the tubular cannula body 602. The one or more notch 612 may be hyperbolic, rectangular, or triangular in shape and configured to interface with the correspondingly shaped tab 508 of the disposable obturator 500. In the illustrative embodiment, two notches 612 are located radially around the posterior end 610 of the tubular cannula body 602, such that the notches 612 are radially separated from one another by 180°. In other embodiments, fewer or greater than two notches 612 are included on the disposable cannula 600. The orientation of the notches 612 may be such that they are radially equidistant around the posterior end 610 of the tubular cannula body 602 from each other, i.e. three notches are separated by 120° each, four notches are separated by 90° each, and so on. In other embodiments, the notches 612 may be oriented radially non-equidistant from one another about the posterior end 610 of the tubular cannula body 602. In all embodiments, the one or more notches 612 are oriented to correspond to the orientation of one or more corresponding tabs 508 of the disposable obturator 500.

In the illustrative embodiment, the disposable cannula 600 further includes a medication slot 614 on a portion of the tubular cannula body 602. The slot 614 is configured or sized to receive a medication pellet and thereby allow the medication pellet access to the interior passage of the disposable cannula 600. The slot 614 may be located anywhere along the tubular body 602 of the disposable cannula 600, such as more proximate to the posterior end 610 of the disposable cannula 600 than a textured handle 616. The textured handle 616 includes hollow recesses forming a honeycombed structure. These hollow recesses may extend fully through the textured handle 616. In another embodiment, these hollow recesses may not extend fully through the textured handle 616, but instead stop at a solid division within the textured handle 616 that forms part of the interior passage of the disposable cannula 600. In some embodiments, the texture arises from cavities or depressions and ridges on the surface of the textured handle 616.

The textured handle 616 may be fixedly coupled to the tubular cannula body 602. The textured handle 616 may be permanently affixed to the exterior of the tubular cannula body 602, removably affixed to the tubular cannula body 602, such as by a snap, clip, collar, threading or chemical means, or may be integral to the disposable cannula 600. Thus, the tubular cannula body 602 and the textured handle 616 may be molded as a single piece.

In the illustrative embodiment, the textured handle 616 and the portions of the disposable cannula located posterior to the textured handle 616, such as the medication slot 614 and posterior cannula end 610, collectively comprise a posterior portion of the disposable cannula 600, while the tubular cannula body 602 comprises an anterior portion of the disposable cannula 600. The posterior portion may be constructed of a plastic material, such as an extruded plastic, that is intended for single use and is disposable, while the anterior portion of the disposable cannula may be constructed from metal, such as aluminum, titanium, or stainless steel. The extruded plastic may be high grade medical plastic, polystyrene (HIPS), acrylonitrile butadiene styrene (ABS), polypropylene (PP), high, low, or linear low density polyethylene (HDPR, LDPE, LLDPE), rigid polyvinyl chloride (PVC), thermoplastics. Further, the extruded plastic may be non-toxic, free of lead, resistant to chemicals, high temperatures (i.e., sterilization temperatures), high wear, and corrosion resistant. The posterior and anterior portions of the disposable cannula may be removably coupled to one another with a snap, clip, collar, or threading.

In the illustrative embodiment, the disposable cannula 600 further includes one or more cannula marking 618 along the tubular cannula body 602. In various embodiments, the cannula markings 618 are visible on the exterior of the tubular cannula body 602. Visibility of the cannula markings 618 may be achieved by scoring, embossing, raising, or coloring. Coloring may include paint, ink, anodizing, or other similarly permanent and visible techniques suitable for use in sterile operations. Where the cannula markings 618 are not scored, embossed, or raised, the cannula markings 618 may be flush with the exterior of the tubular cannula body 602. The cannula markings 618 correspond to a medication length, and serve to aid a doctor or assistant in determining the number of medications or amount of medications administered through the disposable cannula 600. In one embodiment, the cannula markings 618 may be embodied as sunk depressions.

With reference now to FIG. 6B, there is shown the disposable cannula 600 from a side view. This side view shows ergonomic contours on the textured handle 616 designed to conform more closely to an operator's thumb, fingers, and hand. These ergonomic contours in combination with the texture of the handle 616 improve an operator's grip and comfort when handling and using the disposable cannula 600. This view also shows that the outer diameter of the posterior portion of the cannula is larger than the outer diameter of the anterior portion. This disparity in outer diameter size arises from the construction materials used for the illustrative example. In the illustrative cannula, the anterior portion comprises a tube of metal fabrication, while the posterior portion is medical grade plastic. The medical grade plastic construction may require thicker walls, such that an interior diameter that matches for the anterior and posterior portions of the disposable cannula 600 requires that the outer diameter of the posterior portion be larger than that of the anterior portion.

By way of example and not of limitation, the illustrative disposable cannula 600 has a length from the anterior end 606 to the textured handle 616 of between 2 inches and 5 inches, an outer diameter of between 7 mm and 4 mm, and an inner diameter of between 6 mm and 3 mm. In a narrower embodiment, the disposable cannula has a length of between 4½ and 3½ inches, an outer diameter of between 7 mm and 5 mm, and an inner diameter of between 6 mm and 4½ mm. In one embodiment, the disposable cannula length is 4 inches, the outer diameter is 6.6 mm, and the inner diameter is 5.8 mm. In another embodiment, the disposable cannula length is 4 inches, the outer diameter is 5½ mm, and the inner diameter is 5 mm. In another narrow embodiment, the disposable cannula has a length of between 3 and 2 inches, an outer diameter of between 4½ mm and 4 mm, and an inner diameter of between 4 mm and 3½ mm. In one embodiment, the disposable cannula length is 2½ inches, the outer diameter is 4.2 mm, and the inner diameter is 3.7 mm.

Referring now to FIG. 6C, there is shown a perspective view of the disposable cannula 600. This view shows the depth of the hollows comprising the texture of the textured handle 616 and the wall thickness of the posterior portion of the disposable cannula (particularly at the medication slot 614). Additionally, this view shows where the textured handle 616 overlaps with the tubular cannula body 602 in order to facilitate coupling the anterior portion of the disposable cannula and the posterior portion of the disposable cannula. In some embodiments, the snap, clip, collar, or threading are internal to the textured handle 616 that couple the textured handle 616 and posterior portion of the disposable cannula to the tubular cannula body 602 and anterior portion of the disposable cannula.

Figure 7:
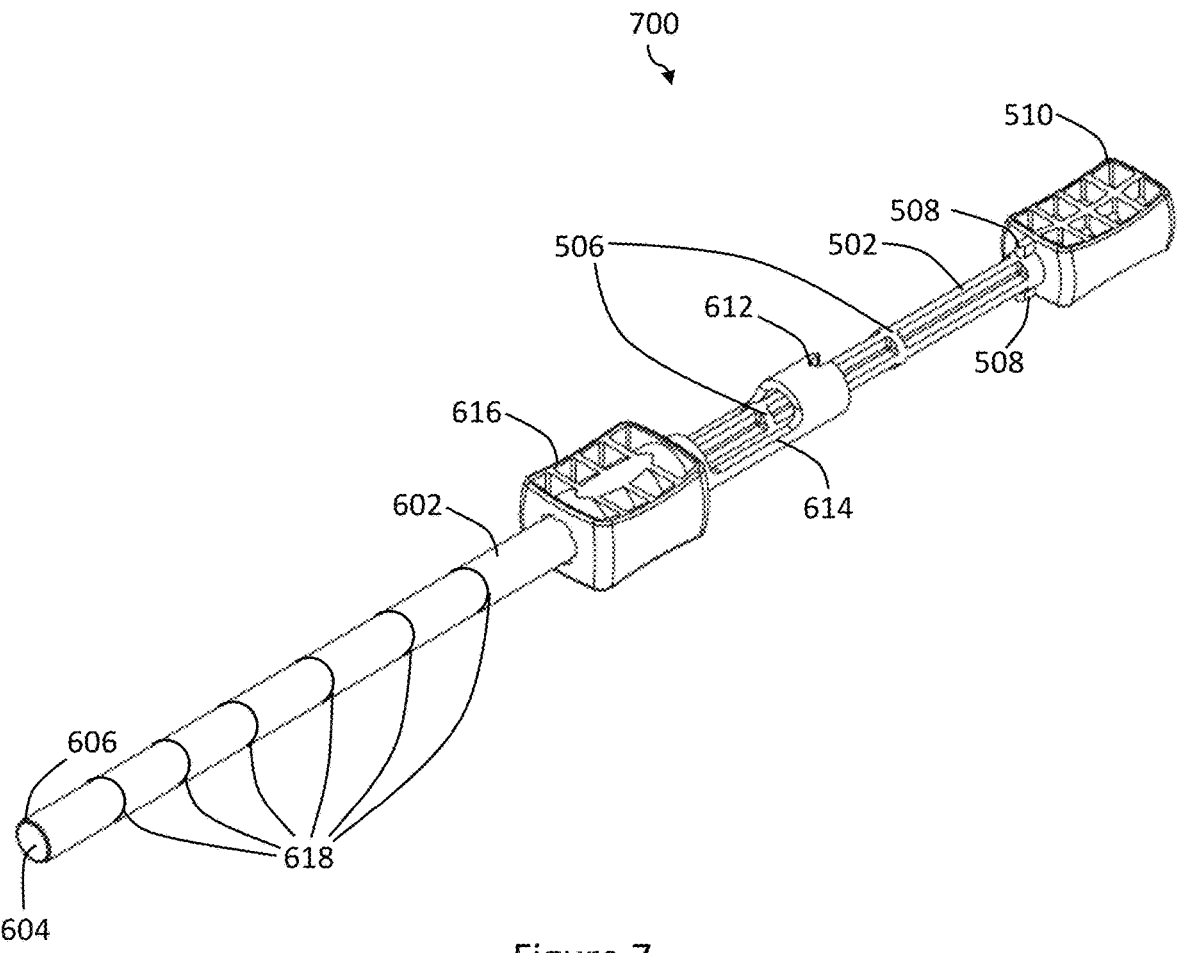
FIG. 7 shows a perspective view of an assembled disposable minimally traumatic trocar.

FIG. 7 shows the disposable cannula 600 and disposable obturator 500 assembled into a disposable minimally traumatic trocar 700. The outer diameter of the tubular obturator body 502 is sized and configured to fit within the interior passage of the disposable cannula tubular body 602 by being 0.001 inches to 0.02 inches less than the inner diameter of the disposable cannula tubular body 602. In the illustrative embodiment, the tolerance (or difference) between the inner diameter of the disposable tubular cannula body 602 and the outer diameter of the disposable tubular obturator body 502 is 0.006 inches. As described above, the solid structure of the obturator obviates the need of a luer lock receptor on the posterior portion of the obturator handle, and provides the user with a more ergonomic grip which makes it easier for the user to manipulate the assembled disposable trocar 700 during subcutaneous insertion.

Figures 8, 9A, 9B, 9C, 9D:
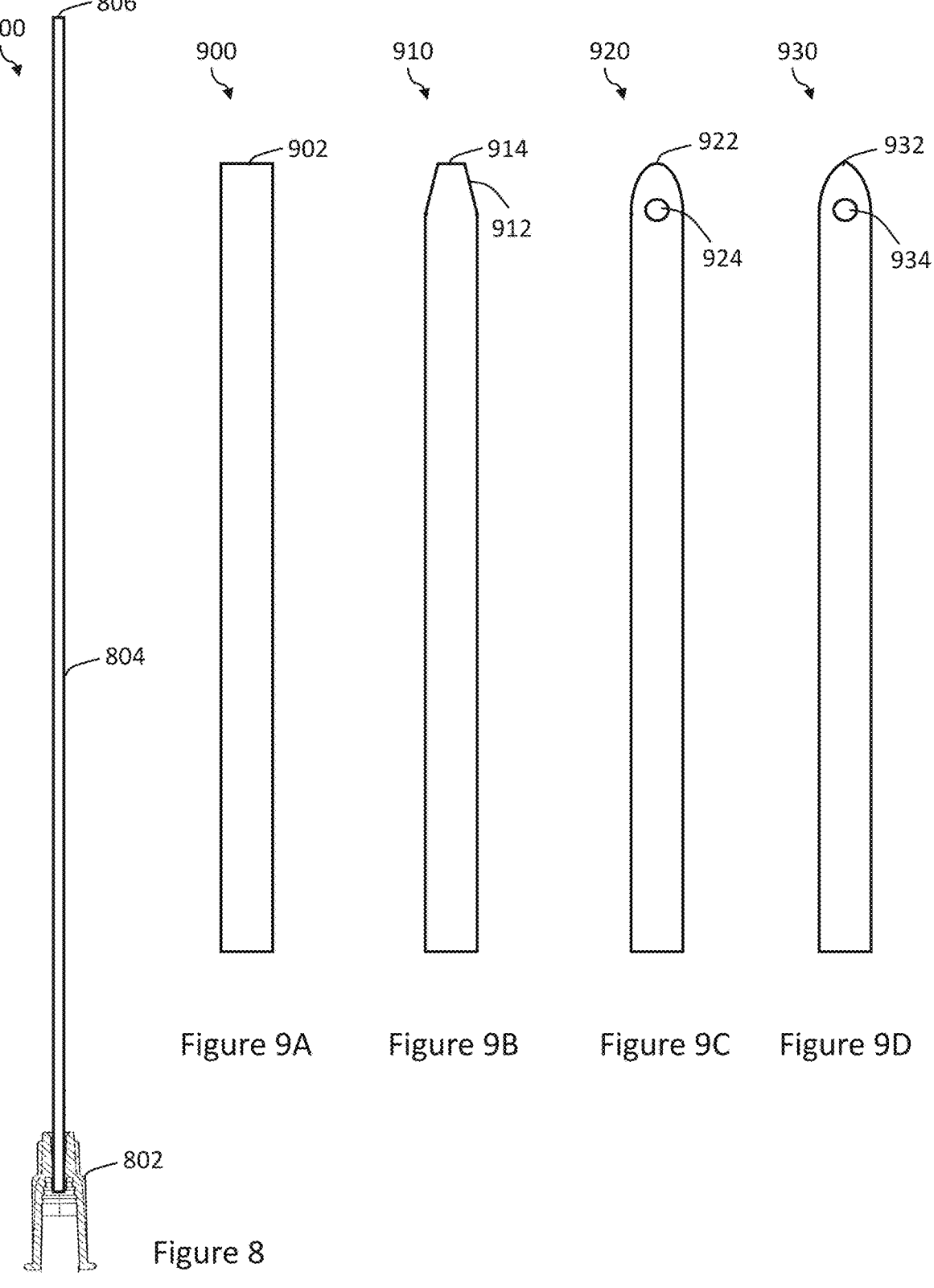
FIG. 8 shows a side view of an illustrative hydrodissection microcannula.
FIG. 9A shows a side view of a 90° blunt microcannula with a terminal opening.
FIG. 9B shows a side view of a conical blunt microcannula with a terminal opening.
FIG. 9C shows a side view of a hyperbolically conical microcannula with side opening.
FIG. 9D shows a side view of a pointed conical microcannula with a side opening.

With reference now to FIG. 8, there is shown an infusion cannula or a hydrodissection microcannula 800. The hydrodissection microcannula 800 includes an attachment hub 802, a shaft 804, and a tip 806. The attachment hub 802 serves to couple the hydrodissection microcannula 800 to a syringe containing a hydrodissection fluid. The attachment hub 802 may include a female luer lock fitting, a polypropylene slip hub, or other comparable fitting for connecting the hydrodissection microcannula 800 to a syringe. The shaft 804 may comprise a medical grade microcannula ranging from 10 gauge (outer diameter=3.4 mm; inner diameter=2.7 mm) down to 30 gauge (outer diameter=3.1 mm; inner diameter=0.16 mm), and have a length ranging from 8 cm to 15 cm. In one embodiment, the hydrodissection microcannula 800 has a length of 10 cm. In another embodiment, the hydrodissection microcannula 800 has a length of 12 cm. The shaft 804 is a hollow tube constructed from biocompatible, pharmacologically inert, non-toxic materials, such as medical grade plastics, stainless steel, carbon steel, nickel plated, and any combination thereof. In the illustrative embodiment, the shaft 804 is a 14 gauge stainless steel construct that is 15 cm long. The tip 806 of the hydrodissection microcannula has an anterior opening or port to the hollow interior of the shaft, and a blunt shape lacking a sharp, beveled, or incising point. Without a surface for a bevel to lie flush against, the bevel would act as a sharp cutting edge. In one embodiment, the hydrodissection microcannula 800 is a polydioxanone (PDO) thread microcannula. In another embodiment, the hydrodissection microcannula 800 is a microcannula.

FIGS. 9A-D shown various types of blunt tip embodiments for the hydrodissection microcannula 800. These types of microcannula tips require an existing incision through the skin into the subcutaneous tissue in order to penetrate along an insertion path and deliver hydrodissection fluid despite a narrow gauge shaft. FIG. 9A shows a microcannula shaft 900 having a flat blunt tip 902 that forms a 90° angle with the length of the shaft 900. The port or opening for hydrodissection fluid is the anterior surface of the tip 902, which is open to the hollow shaft interior.

FIG. 9B shows a microcannula shaft 910 having a conical taper 912 to a flat blunt tip 914 that forms a 90° angle with the length of the shaft 910, but forms an acute angle with the outer surface of the conical taper 912. The port or opening for hydrodissection fluid is the anterior surface of the tip 912, which is open to the hollow shaft interior.

FIG. 9C shows a microcannula shaft 920 having a continuous conical shape coming to a smooth anterior end forming the tip 922. The continuous conical shape is possible in this type of tip because the port or opening 924 for hydrodissection fluid is not located at the anterior terminus of the shaft 920. Instead, this type of microcannula shaft includes the port or opening 924 along the shaft 920, near the anterior terminus of the tip 922. In some embodiments, the port or opening 924 may be situated along the shaft 920 prior to the conical portion of the tip, i.e. situated where the shaft walls are parallel and before the inner and outer diameters begin decreasing to zero at the anterior terminus of the tip 922. In other embodiments, the port or opening 924 may be situated along the shaft 920 where the conical taper of the tip 922 begins, thus the port or opening 924 is situated in part where the shaft walls are parallel and in part on the conical portion of the tip 922. In still other embodiments, the port or opening 924 is located entirely on the conical taper of the tip 922.

FIG. 9D shows a microcannula shaft 930 having a continuous or semi-continuous conical shape coming to a broad pointed anterior end forming the tip 932. The continuous or semi-continuous conical shape is possible in this type of tip because the port or opening 934 for hydrodissection fluid is not located at the anterior terminus of the shaft 930. Instead, this type of microcannula shaft includes the port or opening 934 along the shaft 930, near the anterior terminus of the tip 932. In some embodiments, the port or opening 934 may be situated along the shaft 930 prior to the conical portion of the tip, i.e. situated where the shaft walls are parallel and before the inner and outer diameters begin decreasing to zero at the anterior terminus of the tip 932. In other embodiments, the port or opening 934 may be situated along the shaft 930 where the conical taper of the tip 932 begins, thus the port or opening 934 is situated in part where the shaft walls are parallel and in part on the conical portion of the tip 932. In still other embodiments, the port or opening 934 is located entirely on the conical taper of the tip 932.

Figures 10A, 10B, 10C:
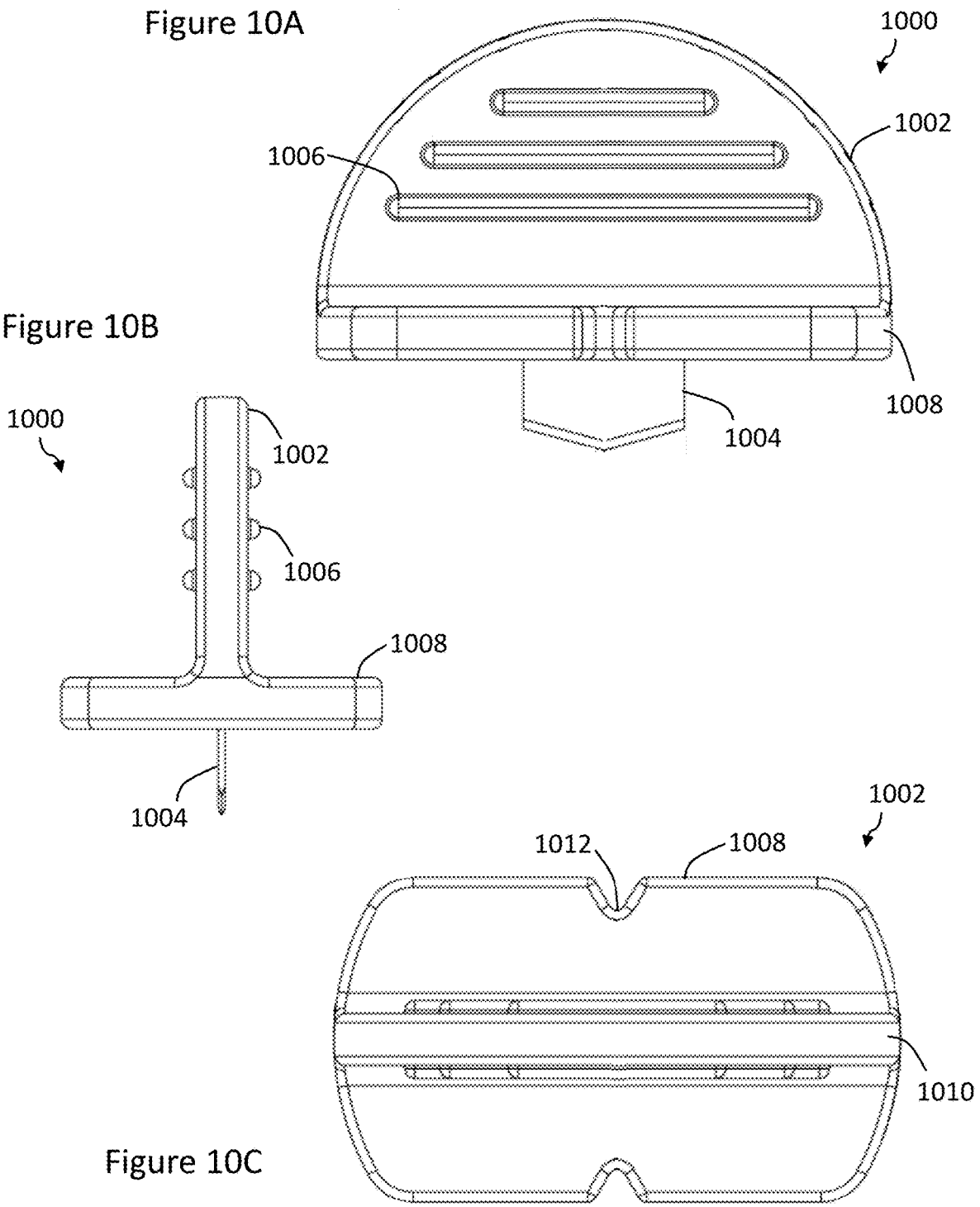
FIG. 10A shows a side view of an illustrative punch scalpel.
FIG. 10B shows an end-on view of the illustrative punch scalpel.
FIG. 10C shows a bottom view of the illustrative punch scalpel.

With reference now to FIGS. 10A-C, there is shown an illustrative punch scalpel 1000 that includes a bracket 1002 and a scalpel blade 1004. Referring now to FIG. 10A, the punch scalpel 1000 is shown from the front. The bracket 1002 houses the scalpel blade 1004 and includes ridges 1006 for a texture grip that allows a doctor or other practitioner to more easily grasp the punch scalpel and therefore improves the overall ergonomic design. In some embodiments, the bracket also includes a base 708 that is perpendicular to the scalpel blade 1004, and enables a stable placement of the punch scalpel on a patient's dermis. In various embodiments, the punch scalpel 1000 can further include a scalpel handle (not shown) extending beyond the scalpel bracket 1002 above and connected to the scalpel blade 1004. In other embodiments, the bracket base is the same width as the bracket.

With reference now to FIG. 10B, there is shown the illustrative punch scalpel from a side view. In the illustrative example, the ridges 1006 are raised above the surface of the bracket 1002. However, in various embodiments, the ridges 1006 may be depressed below the surface of the bracket 1002, or be flush with the surface of the bracket 1002 and have a texture that improves or provides a grip. The bracket base 708 extends beyond the thickness of the bracket 1002 to create a stable platform for a doctor or other practitioner to brace the punch scalpel against the patient's dermis. The scalpel blade 1004 has a thickness that is less than the thickness of the bracket 1002, in order to allow the bracket 1002 to house the scalpel blade 1004.

Referring now to FIG. 10C, there is shown the punch scalpel bracket 1002 from below. The punch scalpel bracket 1002 includes guide slot 1010 that houses the scalpel blade (not shown). Additionally, the base 1008 of the bracket 1002 includes a guide notch 1012 that corresponds to the center of the scalpel blade and the center of any incision made by the scalpel blade.

Figure 11A:
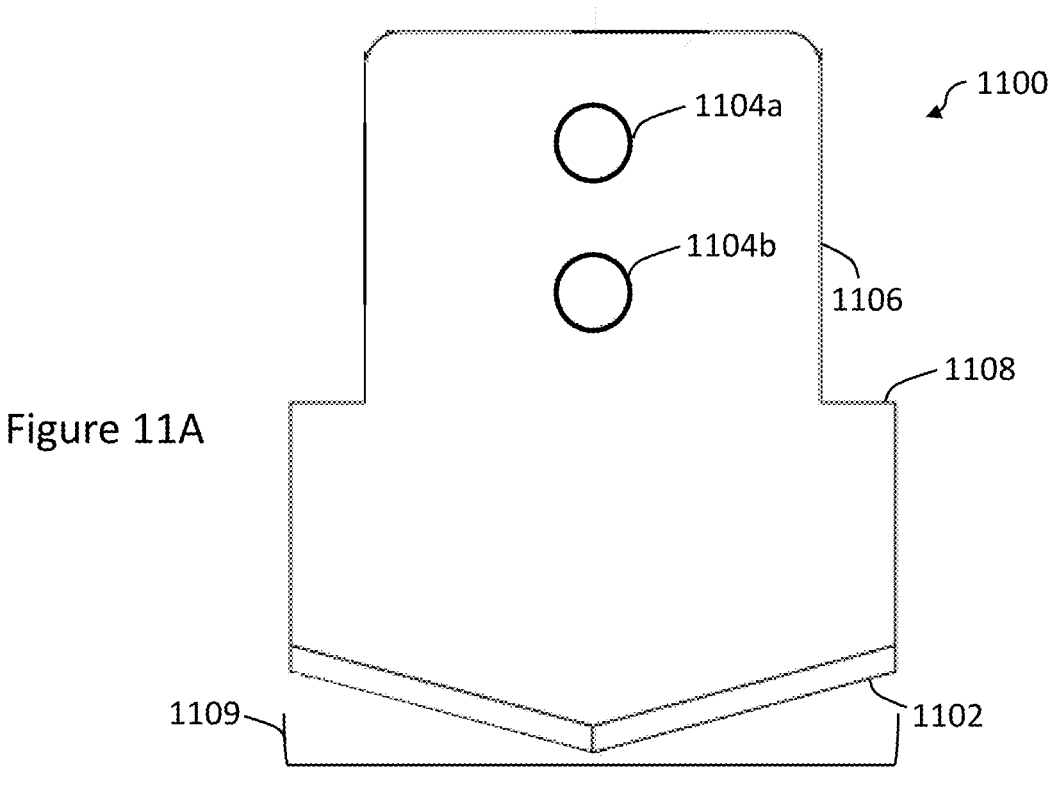
FIG. 11A shows an illustrative punch scalpel blade.
Figure 11B:
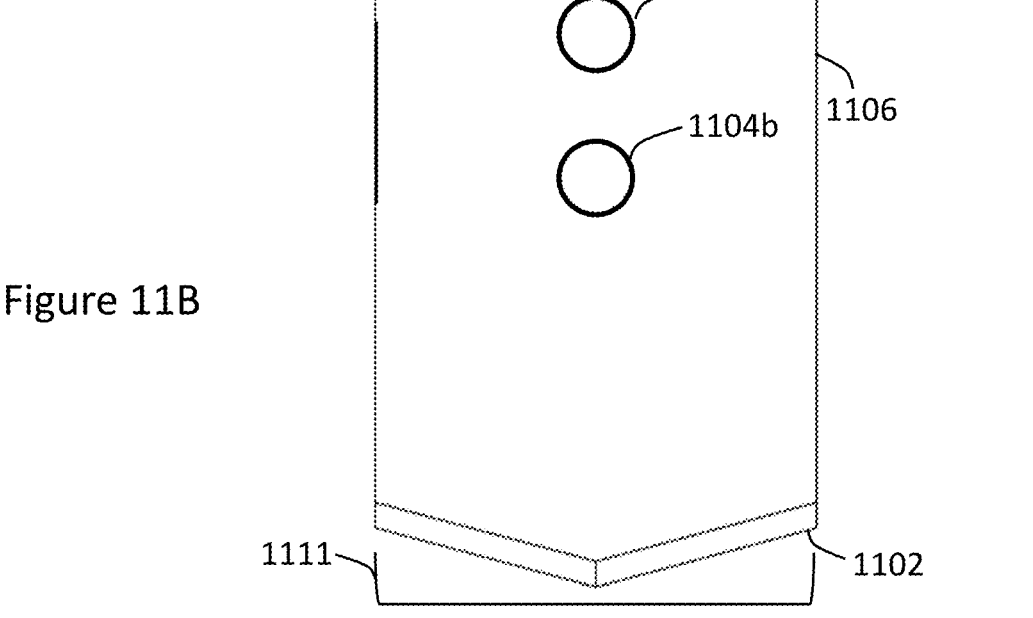
FIG. 11B shows a second illustrative punch scalpel blade.

With reference now to FIGS. 11A and 11B, there is shown illustrative scalpel blades 1100 and 1110, respectively. Both scalpel blades 1100 and 1110 include cutting edges 1102, as well as mounting points 1104*a* and 1104*b* centered within an upper body 1106. Additionally, scalpel blade 1100 includes ledge 1108, which is an artifact arising from the greater width of the scalpel blade edge 1102 with respect to the upper body 1106. The mounting points 1104a and 1104b provide points of attachment for a scalpel handle (not shown) or for guides notches/grooves within the bracket 1002.

In one embodiment, the minimally traumatic trocar kit is a disposable kit that includes the disposable obturator 500, the disposable cannula 600, and instructions informing a user on how to assemble the disposable trocar and deliver pellets to a subcutaneous delivery site, all housed within a disposable packaging. The disposable packaging can be plastic, paper, rigid, flexible, or any combination thereof. In one embodiment, the package is a tray configured to hold the kit elements and a peel-back covering material that seals with the tray, thereby housing the kit elements. The tray may be plastic, cardboard, layered paper, or any other commercially viable material.

The kit elements may comprise the disposable obturator 500, the disposable cannula 600, the hydrodissection microcannula 800, a sterile field drape, antiseptic ointment(s), a syringe, gauze, a scalpel, a cup, forceps, bandages, other wound closure components, and other such materials that may be used during the medical procedure. In an exemplary embodiment, the syringe is a 10 ml syringe for delivering hydrodissection fluid. The scalpel can include an 11 blade scalpel or the punch scalpel 1000. The cup may be plastic, compostable, or otherwise single use. The wound closure components can include butterfly strips, thread and needle (i.e., stitches), or tissue adhesive. The antiseptic ointments can include chlorhexidine sticks, alcohol swabs, and other disinfectants. In an exemplary embodiment, the bandage is a Tegaderm™ transparent film bandage.

Figures 12A, 12B, 12C, 12D:
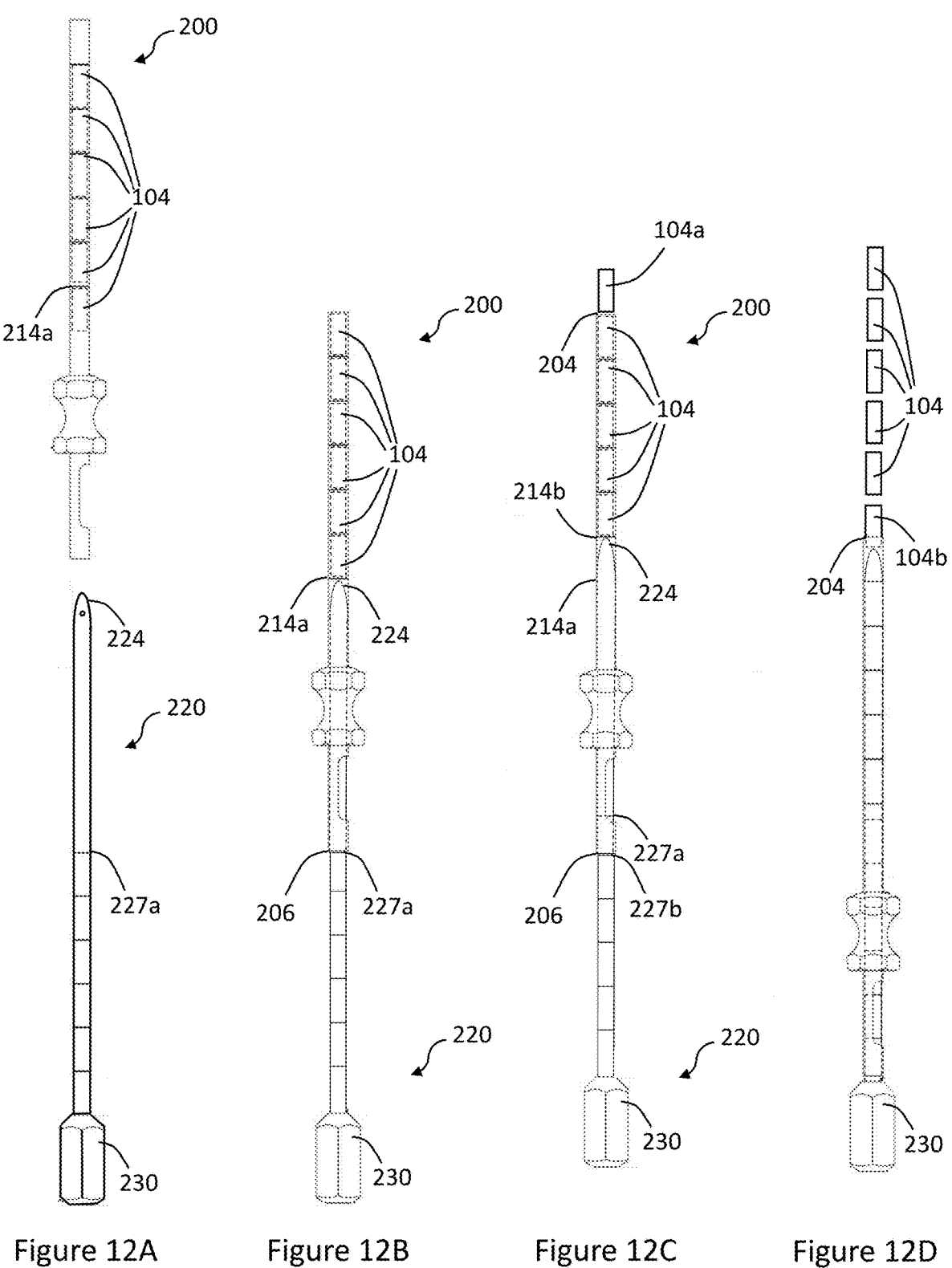
FIG. 12A shows a side view of the illustrative cannula loaded with medication pellets and the obturator immediately prior to displacement and delivery of the medication pellets.
FIG. 12B shows a side view of the illustrative cannula loaded with medication pellets and the obturator inserted into the cannula, pushing the medication pellets into one another and up to an anterior opening of the cannula.
FIG. 12C shows a side view of the illustrative cannula loaded with medication pellets and the obturator inserted into the cannula and pushing the medication pellets into one another so that a first medication pellet is displaced.
FIG. 12D shows a side view of the illustrative obturator fully inserted into the cannula and the pellets fully displaced and extruded as disclosed herein.

With reference now to FIG. 12A, there is shown an illustrative cannula 200 loaded with several medication pellets 104 and an illustrative obturator 220 positioned near the cannula 200 in preparation to deliver the medication pellets 104 by extruding or forcing the pellets 104 through the cannula 200. The length from the most posterior marking 214a on the cannula 200 to the posterior cannula opening 206 and posterior end of the cannula 200 corresponds to the length from the anterior blunt or rounded tip 224 to the most anterior marking 227a on the obturator 220.

Referring now to FIG. 12B, the obturator 220 is inserted into the interior passage of the cannula 200 so that the most anterior marking 227a on the obturator 220 are adjacent to the posterior cannula opening 206. The portion of the obturator 220 that is within the interior passage of the cannula 200 is represented by dotted lines. In this configuration, the blunt tip 224 of the obturator 220 pushes the medication pellets 104 into positions in the interior passage of the cannula 200 corresponding to the cannula markings 214.

Referring now to FIG. 12C, the obturator 220 is inserted into the interior passage of the cannula 200 so that the second most anterior marking 227b on the obturator 220 is adjacent to the posterior cannula opening 206. When the obturator 220 is inserted into the interior passage of the cannula 200 to such a length, the most anterior marking 227a on the obturator 220 is disposed within the interior passage of the cannula 200, the blunt tip 224 of the obturator 220 is aligned with the second most posterior marking 214b of the cannula 200; and the anterior most medication pellet 104a passes through the anterior opening 204 of the cannula 200. This causes the anterior most medication pellet 104a to be delivered to a delivery site.

With reference now to FIG. 12D, the obturator 220 is inserted into the interior passage of the cannula 200 to the full length of the obturator 220, where the obturator handle 230 abuts the posterior opening 206 of the cannula 200. In this configuration, the medication pellets 104 are extruded and delivered even though a portion of the most posterior medication pellet 104b remains within the interior passage of the cannula 200. A portion of the most posterior medication pellet 104b remains within the interior passage of the cannula 200 because this illustrative obturator embodiment has a length that does not extend the blunt tip 224 of the obturator 220 up to or through the anterior opening 204 of the cannula 200 at the anterior end of the cannula 200. The portion of the most posterior medication pellet 104b remaining within the interior passage of the cannula 200 is represented by dotted lines, while the portion of the most posterior medication pellet 104b that has been extruded from or through the anterior opening 204 of the cannula 200 is represented by solid lines. Notably, in embodiments where the obturator is long enough to extend to and/or through the anterior opening of the cannula 204 the most posterior medication pellet 104b is fully ejected from the cannula in to the subcutaneous delivery site. This full ejection/extrusion of the most posterior medication pellet 104b also occurs when the obturator 220 used is long enough to extend through the cannula 200 and out of the anterior cannula opening 204 when inserted into the interior passage of the tubular cannula body 202.

An important feature of the systems and apparatus disclosed by FIGS. 12A-D is that a single obturator 220 is used to insert the atraumatic trocar as well as extrude medication pellets 104 from the interior passage of the cannula 200 for delivery to a delivery site. Notably, prior art trocar apparatus, systems, and methods required the use of a separate delivery obturator because the angled cutting edge on the insertion obturator was not suitable to delivering pellets. The angled cutting edge could cause the pellet and insertion obturator to become stuck in the cannula or shear/shatter the pellet prior to delivery in subcutaneous tissue. However, the rounded anterior tip of the obturator 220 disclosed herein allows for delivery of pellets to subcutaneous tissue through the cannula without concerns that the pellets will shatter or become stuck.

Referring now to FIG. 13, there is shown an illustrative insertion area 1300 and assembled minimally traumatic trocar 1310 having a centerline 1312. The insertion area 1300 is demarcated by the dotted line representing the boundary of an internal cavity of surrounding subcutaneous tissue, and includes an incision site 1302, an insertion path 1304, a delivery site 1306, and a delivery area 1308. The assembled minimally traumatic trocar 1310 follows the insertion path 1304 to the delivery site 1306 by angling the centerline 1312 along an arc 1314 during insertion from a right centerline extreme 1312a to a left centerline extreme 1312b, repeatedly. The insertion path 1304 runs below and approximately parallel to the epidermis tissue layer, through the dermis and ultimately into the subcutaneous tissue, without descending through or below the fascia into muscle, skeletal, or other deeper tissue/organs. The insertion path 1304 may also be described as extending into the incision site 1302, and down through the epidermis and dermis into the subcutaneous tissue. Further still, the insertion path 1304 may be described as traveling parallel and below the epidermis and dermis, as well as through the and within the subcutaneous tissue.

The precise track of the insertion path 1304 will vary with every insertion depending upon the tissue and other connective structures encountered by the assembled minimally traumatic trocar 1310. Thus, the back-and-forth weaving of the assembled minimally traumatic trocar 1310 may oscillate between the right centerline extreme 1312*a* and the left centerline extreme 1312*b* inconsistently, such that the oscillating path varies in both frequency and amplitude. For example, a medical professional operating the assembled minimally traumatic trocar 1310 may direct the assembled minimally traumatic trocar 1310 from the centerline path 1312 directly between the right centerline extreme 1312*a* and the left centerline extreme 1312*b* somewhat towards the right centerline extreme 1312*a* to bounce off a fibrous septa of tissue, then encounter still more connective or other tissue impeding the progress of the assembled minimally traumatic trocar 1310 along that path that requires the medical professional direct the assembled minimally traumatic trocar 1310 further towards the right centerline extreme 1312*a* before avoiding still another portion of denser tissue (such as peripheral somatic nerves or constricted blood vessels, i.e. arterioles or venuoles) which then causes the medical professional to direct the assembled minimally traumatic trocar 1310 back towards the left centerline extreme 1312*b*. In this manner the insertion path 1304 may be irregular and non-linear in order to avoid, slip past, bounce off of, deflect, and prevent trauma or other damage to various tissue structures encountered by the rounded tip.

With reference now to FIG. 14, there are shown medication pellets 104 delivered subcutaneously in the delivery area 1308 through the incision site 1302 on the skin and dermis of a patient from a cannula 200 inserted along the illustrative insertion path 1304. The swerving, curving, and weaving insertion path 1304 allows an assembled minimally traumatic trocar to slip past various connective and fatty tissues causing only micro-trauma and creating a linear space for the cannula 200. The connective and fatty tissues can variously include nerve tissue, blood vessels, arterioles, venuoles, capillaries, and lymphatic tissue. Upon removal of the cannula 200 during medication pellet 104 delivery, the connective and fatty tissues return toward their original position and pushing the delivered medication pellets 104 askew or off-kilter and effectively locking the medication pellets 104 in place in the subcutaneous tissue. Therefore, even though the medication pellets are extruded/delivered from the anterior opening of the cannula 200 along a linear path corresponding to the length of the linear cannula, the medication pellets arrive at final delivery positions within the subcutaneous tissue in a non-linear path as a result of the non-linear insertion path traversed by the assembled minimally traumatic trocar 1310 during insertion. The final delivery positions of the medication pellets may form a delivery pattern along a delivery path that differs from the insertion path taken by the assembled atraumatic trocar. The delivery path runs from the delivery site, where the anterior rounded tip of the obturator reached upon full insertion and where a first medication pellet may be deposited, along a trail formed by the sequentially deposited medication pellets to the incision through which the obturator entered the patient's tissue.

In an alternative embodiment, the non-linear swerving, curving, and/or weaving insertion path 1304 may displace various connective, fatty, and other tissues without causing trauma such that deposited medication pellets are aligned in a linear or near linear pattern (i.e., deposition path) due to the accumulated action and force of the displaced tissues returning toward their original position around the deposited medication pellets.

Figures 15, 16:
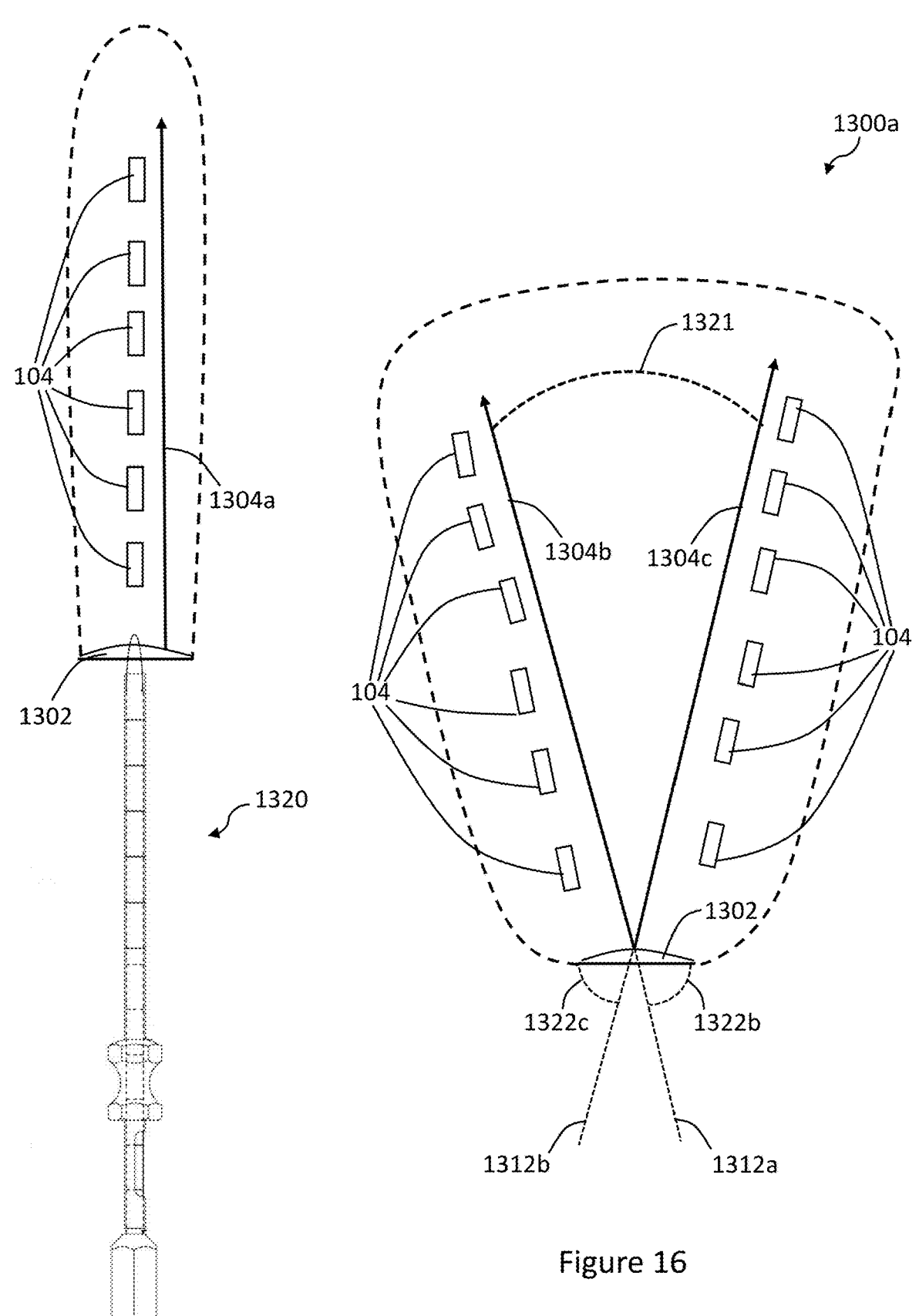
FIG. 15 shows a cut-away view of an illustrative orientation of subcutaneously inserted pellets and assembled minimally traumatic trocar.
FIG. 16 shows a cut-away view of an illustrative orientation of two groups of subcutaneously inserted pellets.

Referring now to FIG. 15, there are shown medication pellets 104 delivered through the incision site 1302 along a linear insertion path 1304*a* and an assembled minimally traumatic trocar 1320. Medication pellets 104 may be spaced evenly, irregularly, or in groups (i.e., two medication pellets close together, adjacent, or abutting, two other medication pellets similarly close to one another but relatively further from the first two medication pellets, and so on). These groups may be of two or more pellets each. Although FIG. 15 shows medication pellets 104 deposited in a nearly perfect linear orientation, the medication pellets 104 may only be in approximately a linear orientation with one or more of the medication pellets 104 being deposited slightly off of the linear centerline.

With reference to FIG. 16, there is shown an insertion area 1300*a* containing two sets of delivered medication pellets 104, wherein the medication pellets 104 are delivered along separate insertion paths 1304*c* and 1304*b*. The separate insertion paths 1304*b* and 1304*c* are separated by an angular distance 1321 corresponding to the angle 1322*c* or 1322*b* at which the centerline 1312*a* and 1312*b* of the assembled minimally traumatic trocar (not shown) was inserted into the incision site 1302 and from which it was removed. In the illustrative embodiment, the sum of angles 1321, 1322*c*, and 1322*b* is 180°. The angles 1322*c* and 1322*b* may be equal or not equal, and may range from a value of 0° through 180°. Thus, the separate insertion paths 1304*b* and 1304*c* form a fan arrangement, and in some embodiments multiple insertion paths may be made between or outside of the insertion paths 1304*b* and 1304*c*. Although the medication pellets of insertion paths 1304*b* and 1304*c* are only approximately linearly deposited, they may each be perfectly or near perfectly linearly deposited. Further, the insertion paths 1304*b* and 1304*c* are not limited to linear embodiments, and may include curved, oscillating, and other non-linear paths.

Figure 17A:
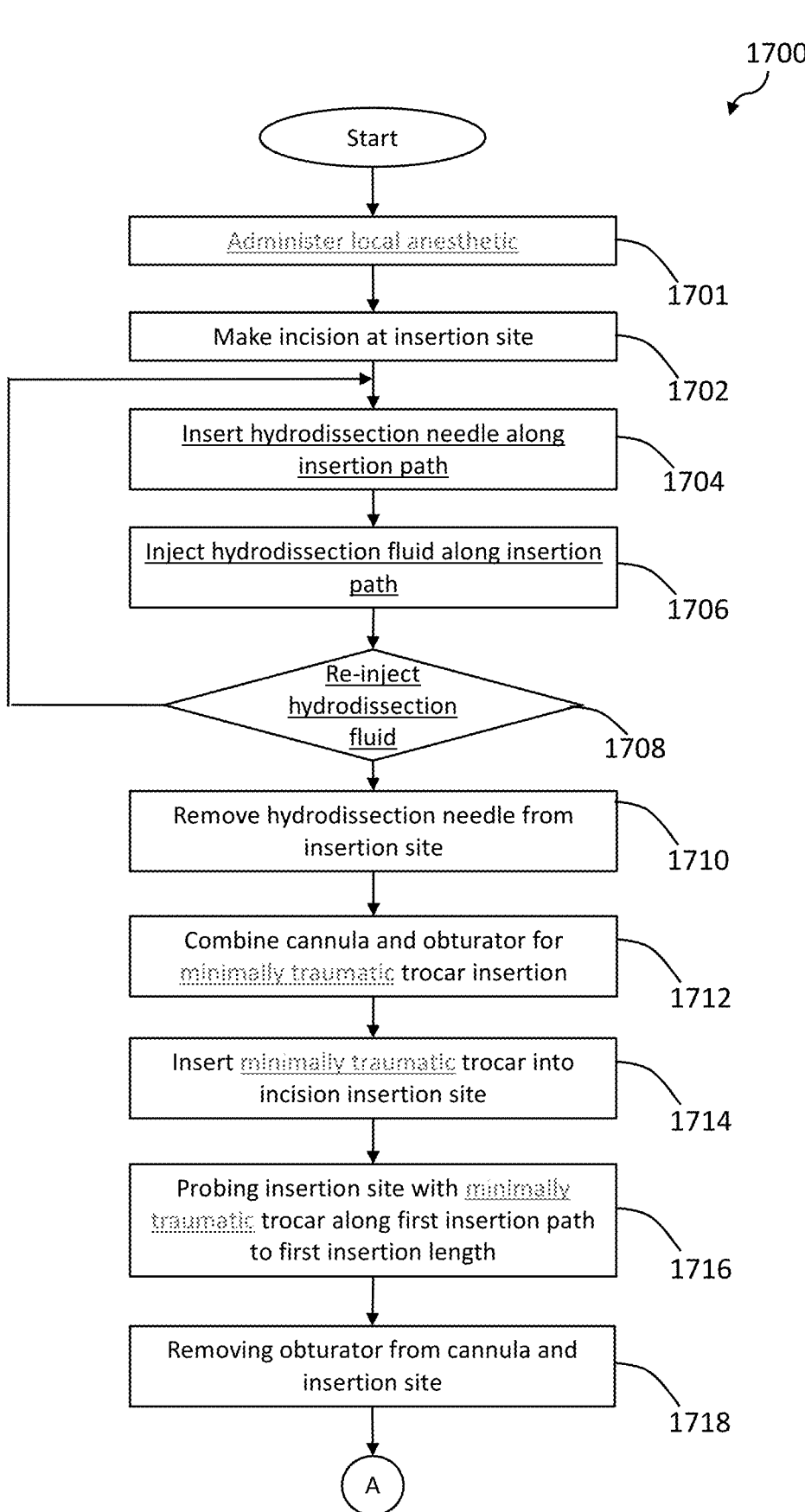
FIGS. 17A, 17B and 17C show an illustrative minimally traumatic subcutaneous pellet insertion method.
Figure 17B:
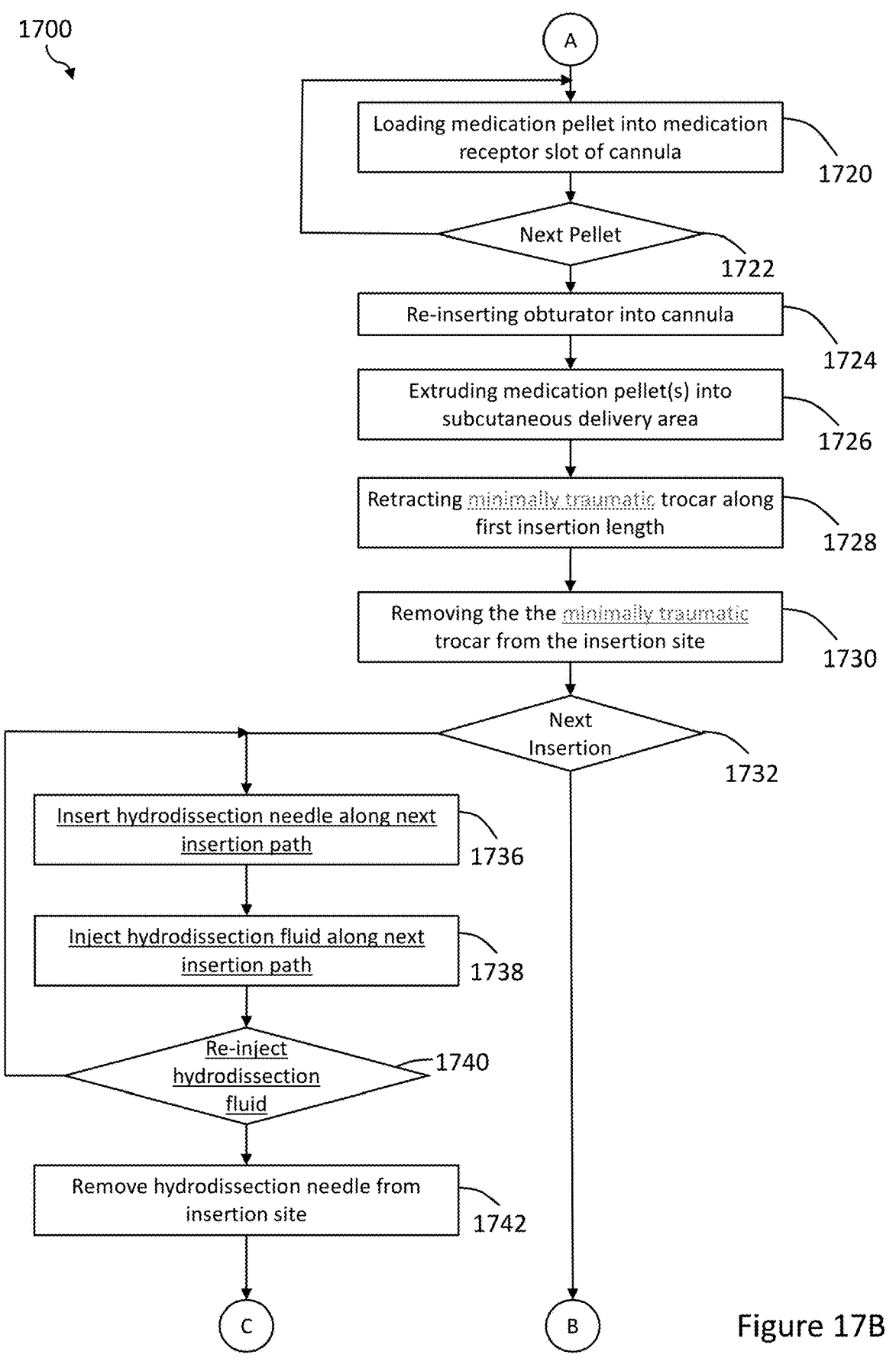
Figure 17C:
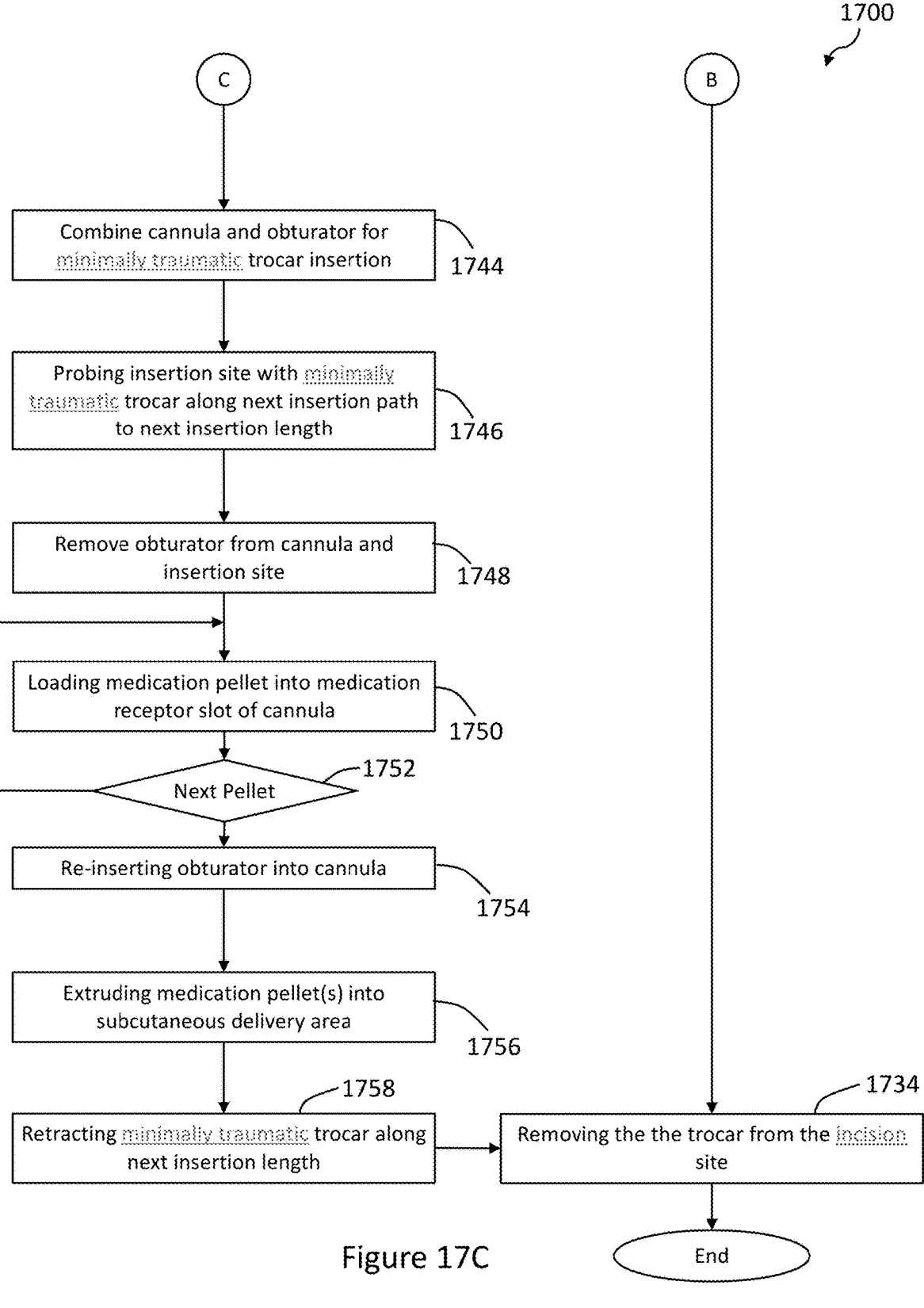

Referring now to FIGS. 17A-C, there is shown a method of subcutaneous medication delivery 1700 causing only minimal micro-trauma. The minimally traumatic trocar used in this and the following steps of the method 1700 may be formed from either the non-disposable cannula 200 and obturator 220 of FIGS. 2A-C, or the disposable cannula 600 and obturator 500 of FIGS. 5 and 6. Where a disposable cannula 600 and obturator 500 are employed, a preliminary step of opening an minimally traumatic trocar kit may be required. In one embodiment, the minimally traumatic trocar kit is disposable and contains a disposable obturator 500, a disposable cannula 600, and a punch scalpel 1000. In further embodiments, the minimally traumatic trocar kit also includes a hydrodissection microcannula 800, scissors, bandages, and antiseptic ointments, as well as instructions informing a user on how to assemble the disposable trocar 700 and deliver pellets to a subcutaneous delivery site.

The method begins in FIG. 17A at step 1701, where local anesthetic is administered to numb the general delivery area or insertion area 1300. The local anesthetic may be topical or one or more injections.

The method 1700 continues at step 1702 by making an incision at an insertion site 1302. The incision can be made with a scalpel or other cutting edge. In some embodiments, the incision is made by the punch scalpel 1000. In operation the punch scalpel base 1008 is placed on a patient's skin at an insertion site. The scalpel blade 1004 is then pressed or plunged into the patient's skin to an incision depth. The incision depth is limited by the punch scalpel bracket. In one embodiment the scalpel blade is plunged into the patient's skin using a scalpel handle attached to the scalpel blade 1000. The incision width is limited to the width of the scalpel blade 1004. In another embodiment, the operator confirms that the scalpel blade 1004 is aligned with the desired insertion site by positioning one or more guide notches 1012 at the desired insertion site. In other embodiments, a preliminary step of diagramming the incision and delivery path(s) is performed, where a medical professional uses a temporary or indelible marking instrument (such as a felt tip pen) to identify both the incision site and the proposed insertion path(s) extending from the insertion site. These markings then operate as a guide for the medical profession during performance of the remaining steps of method 1700.

After making an incision at the insertion site 1302, at step 1704 a blunt tipped hydrodissection microcannula 800 is inserted into the incision, through the epidermis and dermis into the subcutaneous tissue. This insertion begins or creates the insertion path 1304, which the minimally traumatic trocar later follows. The hydrodissection microcannula 800 may be inserted along a linear insertion path to an insertion depth or length. In other embodiments, the hydrodissection microcannula 800 may be inserted along a curved, side-to-side, oscillating, or otherwise non-linear insertion path to an insertion depth or length. In all embodiments, the hydrodissection microcannula 800 is inserted into the incision at an angle that is perpendicular or non-parallel to the surface of the surrounding skin in order to pass through a fascia layer, before being angled parallel to the surface of the surrounding skin and traveling along an insertion path. In one embodiment, the hydrodissection microcannula 800 is inserted into the incision at an angle that is perpendicular or non-parallel to the surface of the surrounding skin in order to pass through a superficial fat cell layer and a scarpa fascia tissue layer to enter a deep fat tissue layer. In the illustrative embodiment, the hydrodissection microcannula 800 is a 14-gauge stainless steel microcannula that is 15 cm long.

At step 1706, during insertion of the hydrodissection microcannula 800 into the incision and along the insertion path 1304, hydrodissecting fluid is injected along the insertion path 1304 into the tissues surrounding the insertion path 1304. The hydrodissecting fluid may comprise a 10 mL dose that is injected at one point of the insertion path, periodically along the insertion path, or continuously along the insertion path. Doses of hydrodissection fluid may range from 1 mL up to 20 mL. Men and women may require different doses generally, i.e. 10 mL for men and 5 mL for women. When the hydrodissecting fluid is injected at only one point of the insertion path, it diffuses into the surrounding subcutaneous tissue, superhydrating the tissue and creating a short dissection plane so that the hydrodissection microcannula 800 may more easily travel through the subcutaneous tissue with only minimal micro-trauma. When the hydrodissecting fluid is injected periodically or continuously along the insertion path, the hydrodissecting fluid superhydrates tissues and creates a dissection plane along the entirety of the insertion path. In all embodiments, the hydrodissection fluid atraumatically enlarges the space or cavity of the delivery site and lubricates the entry of the later assembled minimally traumatic trocar 700 into the various tissues by gently hydrating, softening, and displacing those tissues from the insertion path. In this manner, hydrodissection facilitates easier, simpler, and less painful delivery of the medication pellets. Hydrodissection is especially useful for facilitating insertions into scarred and/or fibrotic tissues, such as tissues that were the site of previous traumatic insertions, and/or repeated insertions.

At decision diamond 1708, a determination is made as to whether additional doses of hydrodissection fluid are required. A medical professional may determine to inject an additional dose of hydrodissection fluid when the initial injection of hydrodissection fluid fails to adequately ease insertion of the hydrodissecting microcannula 800 to a desired length or depth along the insertion path. Such a determination may be made when the initial insertion of the hydrodissection microcannula 800 encounters a blockage or firm tissue that prevents minimally traumatic insertion. Additional doses of hydrodissection fluid may cause the blockage or firm tissue to superhydrate and more easily shift out of the insertion path. In other embodiments, an additional dose of hydrodissection fluid is delivered along a path parallel and adjacent to the first dose to provide a wider insertion path for the later delivered pellets. Additional doses of hydrodissection fluid may require removal of the hydrodissection microcannula 800 or simply the removal of a syringe attached/coupled to the hydrodissection microcannula 800 and replacement with a refilled or second syringe having the additional dose of hydrodissection fluid.

Upon injecting one or more doses of hydrodissection fluid, the method continues at step 1710 where the hydrodissection microcannula 800 is removed from the insertion path and incision. After removal of the hydrodissection microcannula 800, superhydrated subcutaneous tissue surrounding a dissection plane and the insertion path remain.

At step 1712, a blunt edged cannula and round tipped obturator are combined to form a minimally traumatic trocar. The minimally traumatic trocar used in this and the following steps of the method 1700 may be formed from either the non-disposable cannula 200 and obturator 220 of FIGS. 2A-C, or the disposable cannula 600 and obturator 500 of FIGS. 5 and 6. Where a disposable cannula 600 and obturator 500 are employed, a preliminary step of opening a minimally traumatic trocar kit may be required. In one embodiment, the minimally traumatic trocar kit is disposable and contains a disposable obturator 500, a disposable cannula 600, and a punch scalpel 1000. In further embodiments, the minimally traumatic trocar kit also includes a hydrodissection microcannula 800, scissors, bandages, and antiseptic ointments, as well as instructions informing a user on how to assemble the disposable trocar 700 and deliver pellets to a subcutaneous delivery site.

In the illustrative disposable embodiment, the rounded tip 504 of the obturator 500 is inserted into the posterior cannula opening 608 and through the interior passage of the cannula 600, so that the rounded tip 504 extends out through the anterior cannula opening 604. In a further embodiment, the obturator 500 is inserted into the posterior cannula opening 608 so that the tab 508 on the obturator 500 interfaces with the notch 612 of the cannula 600, and causes the assembled disposable minimally traumatic trocar to rotate about the central longitudinal axis as a single unit, i.e. rotating the obturator handle 510 causes the cannula 600 to rotate the same amount, and rotating the cannula handle 616 causes the obturator 500 to rotate the same amount as well. In some embodiments, the medical professional performing the minimally traumatic trocar insertion waits between 1 minute and 10 minutes after completion of hydrodissection with the hydrodissecting microcannula 800 prior to initiating step 1712 by inserting the assembled disposable minimally traumatic trocar 700 into the incision and along the insertion path. In a narrower embodiment, the medical professional performing the minimally traumatic trocar insertion waits 5 minutes after completion of hydrodissection with the hydrodissecting microcannula 800 prior to initiating step 1712 by inserting the assembled disposable minimally traumatic trocar 700 into the incision and along the insertion path. In another embodiment, the medical professional does not wait after completion of the hydrodissection to initiate step 1712, but instead proceeds directly to initiate step 1712.

At step 1714, the assembled minimally traumatic trocar 700 is inserted into the incision site that is also termed an insertion site. The anterior rounded tip 504 of the obturator 500 and thus, the assembled minimally traumatic trocar 700, enters the incision site, followed by the remaining portions of the minimally traumatic trocar 700 as described further below.

At step 1716, the incision site is probed with the assembled minimally traumatic trocar 700 along an insertion path to a predetermined insertion length. The hydrodissection fluid delivered by the hydrodissection microcannula 800 effectively lubricated the insertion path for passage of the assembled minimally traumatic obturator 700 by creating a fluid buffer into which the assembled atraumatic obturator 700 enters, and gently separating the various tissues that are encountered along the insertion path by the assembled minimally traumatic trocar 700 during probing along the insertion path. This lubricating effect softens and hydrates the tissues of the insertion path, easing and improving the maneuverability of the minimally traumatic trocar 700 within the tissue.

The insertion path may be linear or non-linear, and one or more insertion paths may originate at the same insertion site and be angled away from one another in a fan-like orientation to allow the delivery of more medication pellets through a single incision. FIG. 15 demonstrates a linear insertion path 1304*a* followed by the assembled minimally traumatic trocar under the direction of a doctor or other medical professional, FIG. 16 demonstrates angled insertion paths 1304*b* and 1304*c*, and FIGS. 13 and 14 demonstrate an oscillating insertion path 1304. An insertion path may only be angled with respect to another insertion path passing through the same incision site 1302 as the first insertion path. An oscillating insertion path 1304 may be achieved by directing the posterior portion of the assembled minimally traumatic trocar 700 in a side-to-side fashion. The side-to-side, wiggle-waggle, weaving, and/or oscillating motion operates to pass the rounded tip 504 around and past connective tissues in the subcutaneous tissue.

In operation, a doctor or assistant gently pushes the assembled minimally traumatic trocar 700 along an insertion path, moving the posterior portion of the assembled minimally traumatic trocar 700 to one side or the other as the doctor or operator feels resistance from connective tissues and fatty tissues impeding the passage of the minimally traumatic trocar 700 along the insertion path. The predetermined length to which the insertion path is probed may be measured by observing the deformation or bulging of the outer dermis layer caused by the passage of the minimally traumatic trocar 700 passing through the various subcutaneous tissues, i.e. fatty tissue, connective tissue, capillaries, venuoles, arterioles, nerves, etc. In other embodiments, the predetermined length may be measured using the cannula markings 618. Using the cannula markings 618 ensures that the insertion length is sufficient that all of the later loaded medication pellets 104 can be deposited within the subcutaneous tissue or to ensure that the medication pellets 104 are deposited a desired distance from the incision 1302.

At step 1718, the obturator 500 is removed from the cannula 600 and the incision. In one embodiment, the cannula 600 is kept in position, while the obturator 500 is removed. The cannula 600 may be kept in position by holding the cannula handle 616 while the obturator handle 510 is used to remove the obturator 500.

The method 1700 continues in FIG. 17B at step 1720, where a medication pellet 104 is loaded into the interior passage of the cannula 600 through the medication slot 614. In one embodiment, the loaded medication pellet is pushed toward the anterior opening 604 at the anterior end of the cannula 600 with the obturator 500, but not through the anterior opening 604. In another embodiment, the loaded medication pellet is pushed toward the anterior opening 604 at the anterior end of the cannula 600 and through the anterior opening 604.

At decision diamond 1722, a next medication pellet may be loaded into the interior passage of the cannula 600 in the same fashion as the first medication. The next medication pellet 104 can be a second, third, fourth, fifth, sixth, etc. medication pellet depending on the number of previously loaded medication pellets. In one embodiment, when a next pellet is loaded into the interior passage of the cannula 600, the most recently loaded medication pellet is pushed toward the anterior opening 604 at the anterior end of the cannula 600 with the disposable obturator 500. Any next or subsequently loaded medication pellets are pushed through the cannula 600 so that none of the previously loaded medication pellets 104 are extruded through the anterior opening 604 at the anterior end of the cannula 600 and delivered to a delivery area 1308.

At step 1724, the desired number of medication pellets 104 have been loaded into the interior passage of the cannula 600, and the blunt tip 604 of the obturator 500 is inserted into the posterior opening 608 of the cannula 600. The blunt rounded tip 604 of the obturator 500 is passed through the interior passage of the cannula 600 to abut the most posterior loaded medication pellet 104 and push all pellets into a desired position. In one embodiment, the desired position for the medication pellets is for them to be loaded so that the pellets 104 press against and abut one another and align with the cannula markings 618, as well as the anterior opening 604 of the cannula 600.

At step 1726, the loaded medication pellet(s) 104 are extruded through the anterior opening 604 of the cannula 600 and delivered to a subcutaneous delivery area 1308. In one embodiment, the cannula 600 is slowly removed from the incision 1302 as the disposable obturator 500 is inserted further into the interior passage of the cannula 600. By slowly removing the cannula 600 during insertion of the obturator 500, the delivery site 1306 for each successive medication pellet is shifted closer to the incision 1302. Moving the delivery site 1306 of successive pellets allows the medication pellets to be delivered in a linear formation as in FIG. 15, or a snaking, winding or "staggered" formation as in FIGS. 13 and 14, as opposed to the radial clump 130 of the prior art in FIG. 1D. Thus, simultaneous removal of the cannula 600 and insertion or depression of the obturator 500 forces successive medication pellets out of the cannula 600 into a delivery site that is unique for each medication pellet. In some embodiments, complete extrusion of the medication pellets results in full insertion of the obturator 500 into the interior passage of the cannula 600, such that the obturator 500 and cannula 600 are again assembled into the minimally traumatic trocar 700.

At step 1728, the obturator 500 and cannula 600, which may be assembled as the disposable minimally traumatic trocar 700, are retracted along the insertion path toward the incision 1302. In one embodiment, at least one of the anterior rounded tip 504, an anterior portion of the cannula 600, or any combination thereof remains within the incision 1302, while most of the length of the tubular obturator body 502 and the tubular cannula body 602 are removed from the incision 1302. Notably, whether the minimally traumatic disposable trocar 700 was inserted along a linear path as in FIGS. 15 and 16, or a snaking path as in FIGS. 13 and 14, the corresponding minimally traumatic trocar 700 is removed directly, i.e. without any snaking, wiggling, or wagging, such that the removal of the minimally traumatic trocar 700 follows a linear or approximately linear path. In other words, no matter the type of insertion path, the minimally traumatic trocar 700 is retracted with a linear motion along a linear path. As described above, when the insertion path is non-linear, displaced tissue resumes its approximate original location and locks one or more delivered medication pellets in place in the subcutaneous tissue. When the insertion path is linear, tissue may still contract about the delivered medication pellet(s) to hold them in place, although the force of this holding action may be less than when a non-linear insertion path is used.

At step 1730, the disposable obturator 500 is removed from the cannula 600. At decision diamond 1732, a doctor or assistant may determine whether to proceed with a second or next insertion or whether to begin terminating the method. If termination is elected, the method proceeds to step 1734 in FIG. 17C where the cannula 500 or assembled atraumatic trocar 700 is removed from the incision 1302 or the insertion site; the incision 1302 is closed and the method ends. If a second or next insertion is elected, the method proceeds to step 1736.

At step 1736, the blunt tipped hydrodissection microcannula 800 is once again inserted into the incision, through the epidermis and dermis into the subcutaneous tissue. This insertion begins or creates a second insertion path, which the atraumatic trocar later follows. As described above with reference to FIG. 16, the second insertion path begins at the same insertion point as the first insertion path, but extends at an angle to the first insertion path, so that the delivered medication pellets from the first insertion are not immediately adjacent to the pellets that are delivered along the second insertion path. Achieving this requirement that the first and second paths are not immediately adjacent may require an angular separation between the first and second paths of >5°, such as 5°-20°, 20°-40°, 40°-100°, or 100°-180°. The second insertion path along which the hydrodissection microcannula 800 is inserted may be linear and extend to a second insertion depth or length. In other embodiments, the second insertion path of the hydrodissection microcannula 800 may be curved, oscillating, non-linear, or result from an operator moving the posterior end of the atraumatic trocar (and thus the anterior end as well, though in the opposite direction) side-to-side during insertion. In the illustrative embodiment, the hydrodissection microcannula 800 used for the creation of the second insertion path is a 14-gauge stainless steel microcannula that is 15 cm long.

During insertion of the hydrodissection microcannula 800 along the second insertion path at step 1736, hydroddissecting fluid is injected along the second insertion path at step 1738. The hydrodissectin fluid is injected into the tissues surrounding the second insertion path. As with hydrodissection of the first insertion path, the hydrodissecting fluid may comprise a 10 mL dose injected at one point of the second insertion path, periodically along the second insertion path, or continuously along the second insertion path. The dose of hydrodissecting fluid for the second insertion path continues to range from 1 mL up to 20 mL. As with hydrodissection of the first insertion path, the hydrodissecting fluid diffuses into the subcutaneous tissue surrounding the second insertion path, superhydrating that tissue and creating a dissection plane along the second insertion path by enlarging the cavity space created by the passage of the hydrodissection microcannula 800 with only minimal micro-trauma. In some embodiments, the second insertion path lies in the same dissection plane as the first insertion path, such that the first dissection plane and the second dissection plane are the same dissection plane.

Upon injection of one dose of hydrodissecting fluid along the second insertion path, a determination is made at decision diamond 1740 as to whether additional dose(s) of hydrodissection fluid are required. If the operator (or medical professional) determines to inject another dose of hydrodissection fluid, the method reverts back to step 1736 and proceeds as described above.

When a medical professional performing this method has injected one or more doses of hydrodissection fluid and determined that no further administration of hydrodissection fluid are required, the method continues at step 1742 where the hydrodissection microcannula 800 is removed from the second insertion path and incision. After removal of the hydrodissection microcannula 800, superhydrated subcutaneous tissue surrounding a second dissection plane and the second insertion path remain.

The method 1700 continues in FIG. 17C at step 1744, where the cannula 600 and the obturator 500 are again combined to form the minimally traumatic trocar 700. In some embodiments, the same cannula 600 and obturator 500 that were used in steps 1712-1730 is used in step 1744 and the ensuing method steps. In other embodiments, the cannula 600 and obturator 500 that were used in steps 1712-1730 are set aside (disposed of or disinfected) and a new cannula 600 and obturator 500 are retrieved to continue the method 1700. Since the atraumatic trocar 700 is removed from the incision to more readily enable entry of the hydrodissection microcannula 800, an assembled atraumatic trocar 700 must be inserted again into the incision as an assembled unit. Where the cannula 600 and obturator 500 used in steps 1712-1730 are again used, no assembly may be required as the cannula 600 and obturator 500 were removed from the incision as the assembled atraumatic trocar and may remain so until its use at step 1744. Thus, the anterior rounded tip 604 of the obturator first penetrates the dermis and epidermis upon reinsertion, before entering into the subcutaneous tissue within the incision 1302 or insertion site. In a further embodiment, the assembly occurs by inserting the obturator 500 into the posterior cannula opening 608 so that the tab 508 on the obturator 600 interfaces with the notch 612 on the tubular cannula body 602.

In some embodiments, the medical professional performing the minimally traumatic trocar insertion waits between 1 and 10 minutes after completion of hydrodissection with the hydrodissecting microcannula 800 prior to initiating step 1744 by inserting the assembled disposable minimally traumatic trocar 700 into the incision and along the insertion path. In a narrower embodiment, the medical professional performing the minimally traumatic trocar insertion waits 5 minutes after completion of hydrodissection with the hydrodissecting microcannula 800 prior to initiating step 1744 by inserting the assembled disposable minimally traumatic trocar 700 into the incision and along the insertion path. In another embodiment, the medical professional does not wait after completion of the hydrodissection to initiate step 1744, but instead proceeds directly to initiate step 1744.

At step 1746, the assembled trocar 700 is angled away from the previous insertion path and along the second insertion path established by the hydrodissection microcannula 800 in steps 1736-1742, as with the insertion paths 1304*b* and 1304*c* in FIG. 16. The assembled trocar 700 is then used to probe along the length of the next or second insertion path to a predetermined insertion length. This predetermined insertion length may be dependent on the number of medication pellets to be delivered, i.e. a longer insertion length may be desired when more medication pellets are to be delivered. However, it should be noted that even just a single medication pellet may be inserted along an insertion path that is the same length as the insertion path for several pellets. As with the initial insertion path, the second insertion path can be linear or oscillating.

At step 1748, as with step 1718, the obturator 500 is removed from the cannula 600 and the incision 1302, while keeping the cannula 600 in place within the incision 1302 or insertion point.

At step 1750, as with step 1720, a medication pellet 104 is loaded into the interior passage of the cannula 600 through the medication slot 614. In one embodiment, only one medication pellet is loaded into the medication slot.

At decision diamond 1752, as with decision diamond 1722, a next medication pellet may be loaded into the interior passage of the cannula 600 in the same fashion as the first medication pellet, or the method may proceed to step 1754 when the desired number of medication pellets have been loaded into the interior passage of the cannula 600.

At step 1754, as with step 1724, the desired number of medication pellets 104 have been loaded into the interior passage of the cannula 600, and the anterior blunt tip 504 of the obturator 500 is inserted into the posterior opening 608 of the cannula 600. The anterior rounded tip 504 of the obturator 500 is passed through the interior passage of the cannula 600 to abut the most posterior loaded medication pellet 104 and push all pellets into a desired position within the cannula 600.

At step 1756, as with step 1726, the loaded medication pellet(s) 104 are extruded through the anterior opening 604 of the cannula 600 and delivered to a second subcutaneous delivery site within the general delivery area. The delivery area may include both the first delivery site and the second delivery site.

At step 1758, as with step 1728, the assembled minimally traumatic trocar 700 is retracted along the second insertion path toward the incision 1302. In one embodiment, at least an anterior portion of the cannula 600 remains within the incision 1302, allowing the method to either terminate at step 1734 or return to decision diamond 1732 and continue with the establishment of a third or next insertion path for reception of a third set of medication pellet(s).

At step 1734, the cannula 600 or assembled minimally traumatic trocar 700 is removed from the incision 1302, the incision 1302 is closed and the method 1700 ends. The incision 1302 may be closed with stitches, medical glue, butterfly bandage, or similar bandaging means.

Figure 18A:
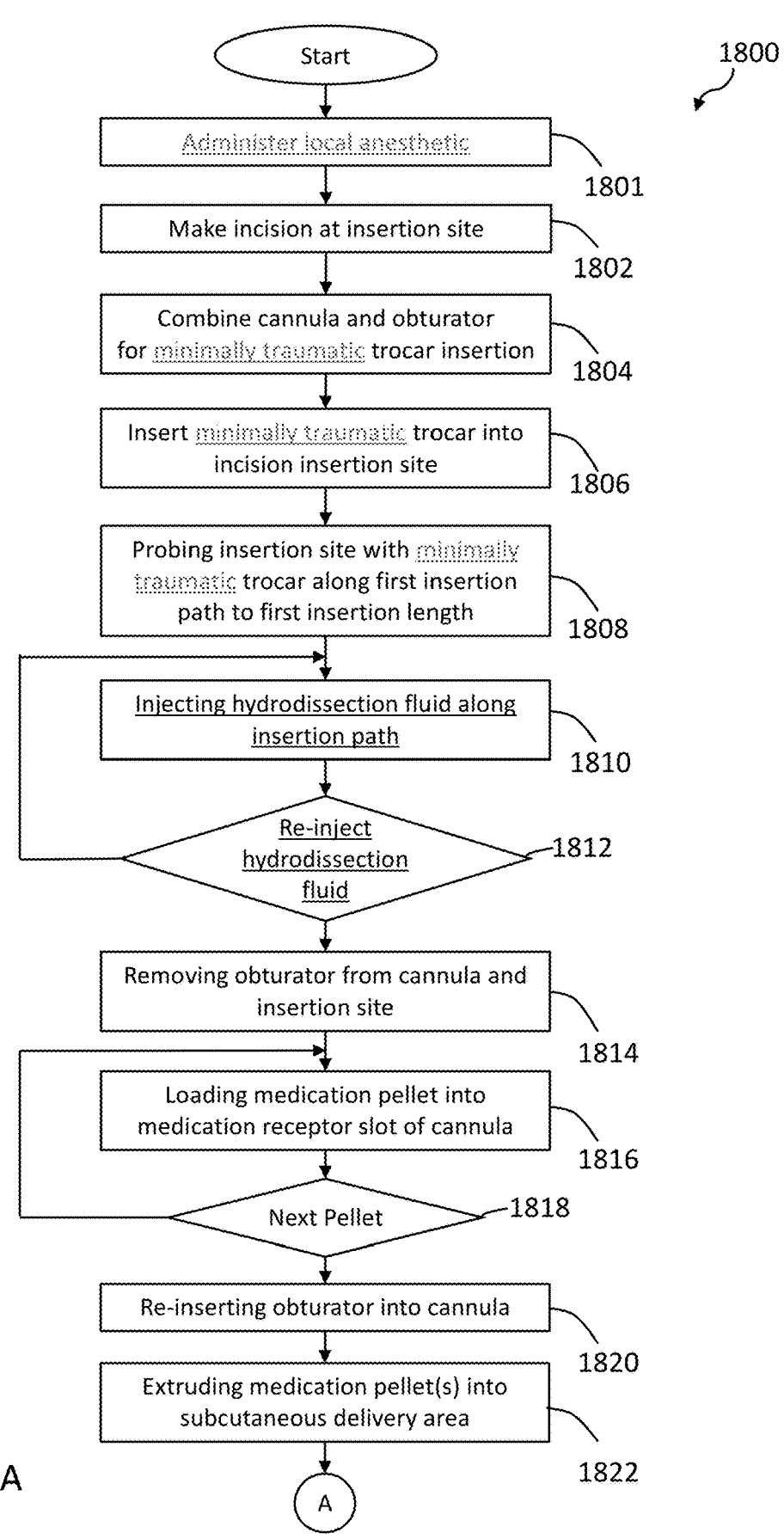
FIGS. 18A and 18B show a second illustrative minimally traumatic subcutaneous pellet insertion method.
Figure 18B:
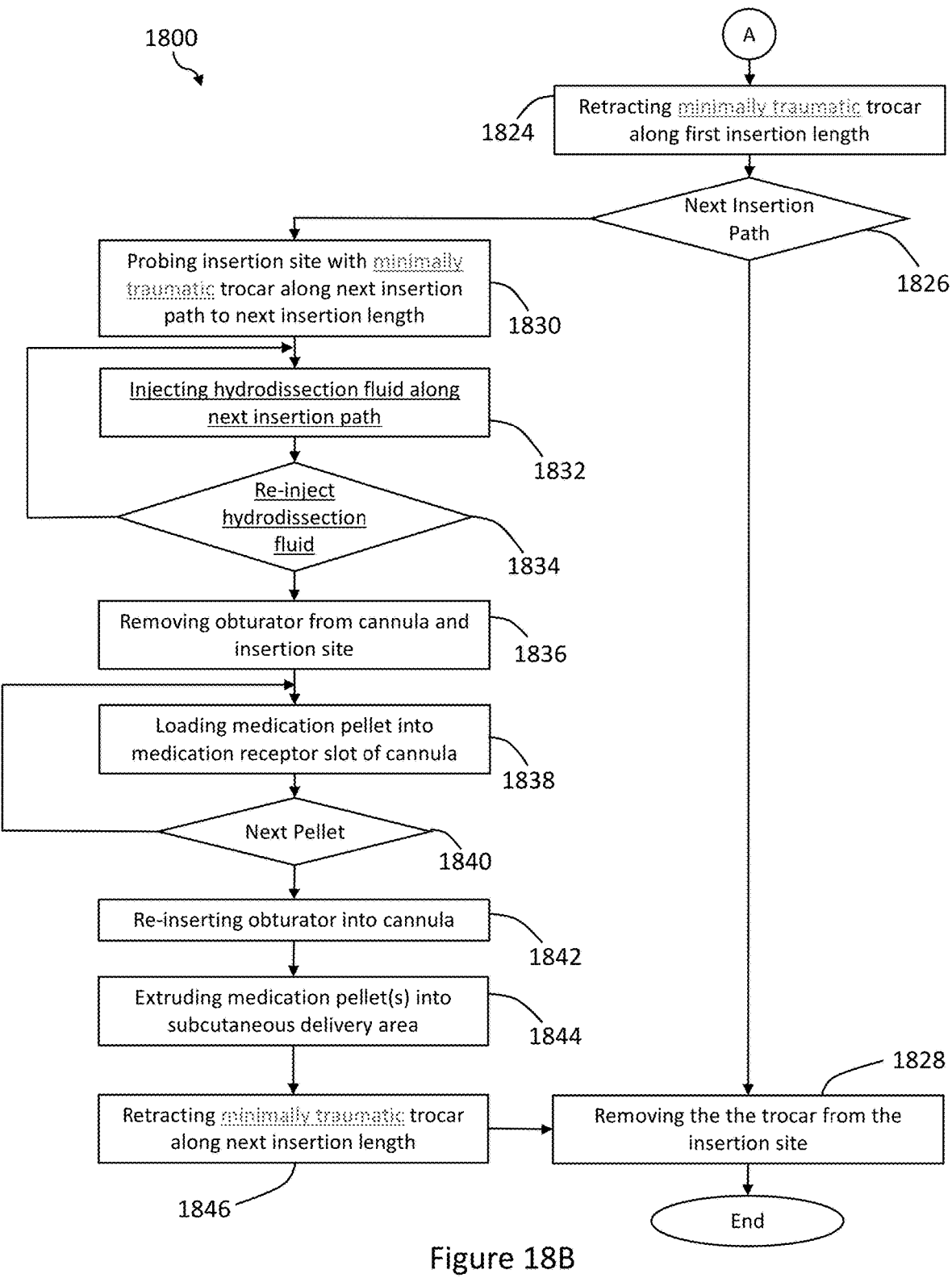

Referring now to FIGS. 18A-B, there is shown another method of subcutaneous medication delivery 1800 causing only minimal micro-trauma. The method 1800 begins in FIG. 18A at step 1801, where local anesthetic is administered to numb the general delivery area or insertion area 1300. The local anesthetic may be topical or one or more injections.

The method 1800 continues at step 1802 by making an incision at an insertion site 1302. This incision 1302 can be made with a scalpel or other cutting edge. In some embodiments, the incision 1302 is made by the punch scalpel 1000. In other embodiments, a preliminary step of diagramming the incision and delivery path(s) is performed, where a medical professional uses a temporary or indelible marking instrument (such as a felt tip pen) to identify both the incision site and the proposed insertion path(s) extending from the insertion site. These markings then operate as a guide for the medical profession during performance of the remaining steps of method 1800.

At step 1804, a blunt edged cannula and round tipped obturator are combined to form a minimally traumatic trocar. The minimally traumatic trocar used in this and the following steps of the method 1800 may be formed from the disposable cannula and obturator disclosed in FIGS. 5A and 5C of the cross-referenced non-provisional patent application Ser. No. 16/997,803. In the illustrative embodiment described herein, the minimally traumatic trocar used in this and the following steps of the method 1800 may be the non-disposable trocar 240 formed from the non-disposable cannula 200 and obturator 220 of FIGS. 2A-C. In the illustrative non-disposable embodiment, the rounded tip 224 of the obturator 220 is inserted into the posterior cannula opening 206 and through the interior passage of the cannula 200, so that the rounded tip 224 extends out through the anterior cannula opening 204. In a further embodiment, the obturator 220 is inserted into the posterior cannula opening 206 so that the tab 232 on the obturator 220 interfaces with the notch 212 on the tubular cannula body 202, and causes the assembled minimally traumatic trocar 240 to rotate about the centerline 1312 of the minimally traumatic trocar as a single unit, i.e. rotating the obturator handle 230 causes the cannula 200 to rotate the same amount, and rotating the cannula handle 210 causes the obturator 220 to rotate the same amount as well.

At step 1806, the assembled minimally traumatic trocar 240 is inserted into the incision site 1302. The anterior rounded tip 224 of the obturator 220 and thus, the assembled minimally traumatic trocar 240, enters the incision 1302, followed by the remaining portions of the minimally traumatic trocar 240 as described further below.

At step 1808, the incision 1302 is probed with the assembled minimally traumatic trocar 240 along an insertion path to a predetermined insertion length. The insertion path may be linear or non-linear, and one or more insertion paths may originate at the same insertion/incision site and be angled away from one another in a fan-like orientation to allow the delivery of more medication pellets through a single incision. FIG. 15 demonstrates a linear insertion path 1304*a* followed by the assembled minimally traumatic trocar 240 under the direction of a doctor or other medical professional, FIG. 16 demonstrates angled insertion paths 1304*b* and 1304*c*, and FIGS. 13 and 14 demonstrate an oscillating insertion path 1304. An insertion path may only be angled with respect to another insertion path passing through the same incision 1302 as the first insertion path. An oscillating insertion path 1304 may be achieved by directing the posterior portion of the assembled minimally traumatic trocar 240 in a side-to-side fashion. The side-to-side, wiggle-waggle, weaving, and/or oscillating motion operates to pass the rounded tip 224 around and past connective tissues in the subcutaneous tissue.

In operation, a doctor or medical professional gently pushes the assembled minimally traumatic trocar 240 along an insertion path, moving the posterior portion of the assembled minimally traumatic trocar 240 to one side or the other as the operator feels resistance from connective tissues and fatty tissues impeding the passage of the minimally traumatic trocar 240 along the insertion path. The predetermined length to which the insertion path is probed may be measured by observing the deformation or bulging of the outer dermis layer caused by the passage of the minimally traumatic trocar 240 passing through the various subcutaneous tissues, i.e. fatty tissue, connective tissue, capillaries, venuoles, arterioles, nerves, etc. In other embodiments, the predetermined length may be measured using the cannula markings 214. Using the cannula markings 214 ensures that the insertion length is sufficient that all of the later loaded medication pellets 104 can be deposited within the subcutaneous tissue or to ensure that the medication pellets 104 are deposited a desired distance from the incision 1302 or insertion site.

At step 1810, the assembled trocar 240 delivers a particular agent (i.e., a numbing solution, anesthetic, and/or hydrodissection fluid) to the tissue along the insertion path through openings 228 in the obturator 220 during the probing of step 1808. One of these openings 228 may be located at or comprise the most anterior portion of the anterior blunt tip 224 of the obturator 220, so that the delivered agent is the first element of the assembled minimally traumatic trocar 240 to contact tissues along the insertion path. Alternatively, or in addition to this configuration, the obturator 220 may include one or more openings proximal to the anterior rounded tip (as shown in FIGS. 2B and 3A-E) that deliver the agent to tissues adjacent to the anterior rounded tip 224 and the tubular body 222 of the obturator 220 and tubular cannula body 202. The delivered agent effectively lubricates the passage of the assembled minimally traumatic trocar 240 by creating a fluid buffer around the assembled minimally traumatic trocar 240 and gently separating the various tissues encountered by the assembled minimally traumatic trocar 240 during probing along an insertion path. This lubricating effect softens and hydrates tissues encountered, easing and improving the maneuverability of the minimally traumatic trocar within the tissue.

Where the delivered agent is hydrodissecting fluid, the hydrodissecting fluid may comprise a 10 mL dose that is injected at one point of the insertion path, periodically along the insertion path, or continuously along the insertion path. Doses of hydrodissection fluid may range from 1 mL up to 20 mL. When the hydrodissecting fluid is injected at only one point of the insertion path, it diffuses into the surrounding subcutaneous tissue, superhydrating the tissue and creating a short dissection plane so that the assembled atraumatic trocar 240 may more easily travel through the subcutaneous tissue with minimal amounts of micro-trauma. When the hydrodissecting fluid is injected periodically or continuously along the insertion path, the hydrodissecting fluid superhydrates tissues and creates a dissection plane along the entirety of the insertion path. In all embodiments, the hydrodissection fluid enlarges the space or cavity of the delivery site and lubricates the entry of the assembled atraumatic trocar 240 into the various tissues with minimal micro-trauma by gently hydrating, softening, and displacing those tissues from the insertion path. In this manner, hydrodissection facilitates easier, simpler, and less painful delivery of the medication pellets.

In these embodiments, the particular agent (i.e., one or more numbing solutions, such as anesthetics and/or hydrodissection fluids) may be delivered through only two openings proximate to the anterior rounded tip 224 of the obturator 220, or through openings that spiral along the length of the portion of the obturator tubular body 222 that extends beyond the anterior opening of the cannula 204. The inventor hypothesizes that the various agents create a fluid channel about the assembled minimally traumatic trocar 240, and thereby enlarges the space or cavity of the delivery site with minimal amounts of micro-trauma and facilitates delivery of the medication pellets. The inventor further hypothesizes that hydrodissection facilitates insertion into scarred and/or fibrotic tissues, such as tissues that were the site of previous traumatic insertions, and/or repeated insertions.

At decision diamond 1812, a determination is made as to whether additional doses of the particular agent or hydrodissection fluid are required. A medical professional may determine to inject an additional dose, such as of hydrodissection fluid, when the initial administration of hydrodissection fluid fails to adequately ease insertion of the minimally traumatic trocar 240 to a desired length or depth along the insertion path. Such a determination may be made when the initial insertion of the minimally traumatic trocar 240 encounters a blockage or firm tissue that prevents minimally traumatic insertion. A blockage preventing minimally traumatic insertion of the trocar 240 would require the surrounding and/or blocking tissue to tear, rupture, and/or inflame for the minimally traumatic trocar 240 to pass through the tissue. Additional doses of hydrodissection fluid may cause the blockage or firm tissue to superhydrate and more easily shift out of the insertion path. Additional doses of hydrodissection fluid may be administered through a syringe removably coupled to the threaded posterior end 234 of the obturator 220. In practice, a medical professional may inject a further dose of hydrodissection fluid through the minimally traumatic trocar 240 into the blocking tissue and/or surrounding tissue with the same syringe used to inject the first dose of hydrodissection fluid into the tissues of the insertion path. This further dose may be 10 mL of hydrodissection fluid that remain in the syringe after an initial dose of 10 mL of hydrodissection fluid, i.e. the syringe originally held 20 mL. In other embodiments, the syringe may be decoupled from the minimally traumatic trocar 240 in order to retrieve another 10 mL dose of hydrodissection fluid. Additional doses of hydrodissection fluid administered through the minimally traumatic trocar 240 may be dispensed from the obturator openings 228 into the tissues at or surrounding one point of the insertion path, several points along the insertion path, and/or continuously along the insertion path.

Upon injecting one or more doses of hydrodissection fluid, the method continues at step 1814, the obturator 220 is removed from the cannula 200 and the incision 1302. In one embodiment, the cannula 200 is kept in position, while the obturator 220 is removed. The cannula 200 may be kept in position by holding the cannula handle 210 while the obturator handle is used to remove the obturator 220.

At step 1816, a medication pellet 104 is loaded into the interior passage of the cannula 200 through the medication slot 208. In one embodiment, the loaded medication pellet is pushed toward the anterior opening 204 at the anterior end of the cannula 200 with the obturator 220, but not through the anterior opening 204. In another embodiment, the loaded medication pellet is pushed toward the anterior opening 204 at the anterior end of the cannula 200 and through the anterior opening 204 into the subcutaneous tissue surrounding the delivery site 1306, and/or along the insertion path 1304 (i.e. the delivery area 1308).

At decision diamond 1818, a next medication pellet may be loaded into the interior passage of the cannula 200 in the same fashion as the first medication. The next medication pellet 104 can be a second, third, fourth, fifth, sixth, etc. medication pellet depending on the number of previously loaded medication pellets. In one embodiment, when a next pellet is loaded into the interior passage of the cannula 200, the most recently loaded medication pellet is pushed toward the anterior opening 204 at the anterior end of the cannula 200 with the obturator 220. Any next or subsequently loaded medication pellets are pushed through the cannula 200 so that none of the previously loaded medication pellets are extruded through the anterior opening 204 at the anterior end of the cannula 200 and delivered to a delivery area 1308.

At step 1820, the desired number of medication pellets 104 have been loaded into the interior passage of the cannula 200, and the anterior blunt tip 224 of the obturator 220 is inserted into the posterior opening 206 of the cannula 200. The blunt tip 224 of the obturator 220 is passed through the interior passage of the cannula 200 to abut the most posterior loaded medication pellet 104 and push all pellets into a desired position. In one embodiment, the desired position for the medication pellets is as depicted in FIG. 12B, where the loaded pellets 104 pressed to abut one another and align with the cannula markings 214, as well as the anterior opening 204 of the cannula 200.

At step 1822, the loaded medication pellet(s) 104 are extruded through the anterior opening 204 of the cannula 200 and delivered to a subcutaneous delivery area 1308. In one embodiment, the cannula 200 is slowly removed from the incision 1302 as the obturator 220 is inserted further into the interior passage of the cannula 200. By slowly removing the cannula 200 during insertion of the obturator 220, the delivery site 1306 for each successive medication pellet is shifted closer to the incision 1302. Moving the delivery site 1306 of successive pellets allows the medication pellets to be delivered in a linear formation as in FIGS. 15 and 16, or a snaking, winding or "staggered" formation as in FIGS. 13 and 14, as opposed to the radial clump 130 of the prior art in FIG. 1D. Thus, simultaneous removal of the cannula 200 and insertion or depression of the obturator 220 forces successive medication pellets out of the cannula 200 into a delivery site that is unique for each medication pellet. In some embodiments, complete extrusion of the medication pellets results in full insertion of the obturator 220 into the interior passage of the cannula 200, such that the obturator 220 and cannula 200 are again assembled into the minimally traumatic trocar 240.

At step 1824, the obturator 220 and cannula 200, which may be assembled as the minimally traumatic trocar 240, are retracted along the insertion path toward the incision 1302. In one embodiment, at least one of the anterior rounded tip 224, an anterior portion of the cannula 200, or any combination thereof remains within the incision 1302 while most of the length of the tubular obturator body 222 and the tubular cannula body 202 are removed from the incision 1302. Notably, whether the minimally traumatic trocar 240 was inserted along a linear path as in FIGS. 15 and 16, or a snaking path as in FIGS. 13 and 14, the corresponding minimally traumatic trocar 240 is removed directly, i.e. without any snaking, wiggling, or wagging, such that the removal of the minimally traumatic trocar 240 follows a linear or approximately linear path. In other words, no matter the type of insertion path, the minimally traumatic trocar 240 is retracted with a linear motion along a linear path. As described above, when the insertion path is non-linear, displaced tissue resumes its approximate original location and locks one or more delivered medication pellets in place in the subcutaneous tissue. When the insertion path is linear, tissue may still contract about the delivered medication pellet(s) to hold them in place, although the force of this holding action may be less than when a non-linear insertion path is used.

At decision diamond 1826, a doctor or other medical professional may determine whether to proceed with a second or next insertion or whether to begin terminating the method. If termination is elected, the method proceeds to step 1828 where the cannula 200 or assembled minimally traumatic trocar 240 is entirely removed from the incision 1302 site; and the incision 1302 is closed such that the method ends. If a second or next insertion is elected, the method proceeds to step 1830.

At step 1830, an assembled trocar 240 is angled away from the previous insertion path, as with the insertion paths 1304b and 1304c in FIG. 16, towards a next or second insertion path. The second insertion path begins at the same insertion point as the first insertion path, but extends at an angle to the first insertion path, so that the delivered medication pellets from the first insertion are not immediately adjacent to the pellets that are delivered along the second insertion path. Achieving this requirement that the first and second paths are not immediately adjacent may require an angular separation between the first and second paths of >5°, such as 5°-20°, 20°-40°, 40°-100°, or 100°-180°. The assembled trocar 240 is then used to probe along the length of the next or second insertion path to a predetermined insertion length. This predetermined insertion length may be dependent on the number of medication pellets to be delivered, i.e. a longer insertion length may be desired when more medication pellets are to be delivered. However, it should be noted that even just a single medication pellet may be inserted along an insertion path that is same length as the insertion path for several pellets. As with the initial insertion path, the second insertion path can be linear or oscillating, but must be angle away from the initial insertion path.

Step 1830 may additionally require the assembly of another minimally traumatic trocar if the minimally traumatic trocar used for the initial insertion of medication pellets is not used for the subsequent insertion. In an alternative embodiment, step 1830 may require the re-assembly of the minimally traumatic trocar 240 used in the initial insertion of medication pellets if the obturator 220 was not fully inserted into the interior passage of the cannula 200 during retraction along the insertion path in step 1824. Where re-assembly of the obturator 220 and cannula 200 is necessary, the operator may need to perform the re-assembly ex vivo and re-insert the re-assembled minimally traumatic trocar 240 into the incision 1302. Alternatively, re-assembly may occur while at least one of the anterior rounded tip 224, an anterior portion of the cannula 200, or any combination thereof remains within the incision 1302, which does not require re-insertion of the assembled minimally traumatic trocar 240 into the incision 1302 (as a portion of it remained within the incision).

At step 1832, the assembled trocar 240 delivers a particular agent (i.e., a numbing solution, anesthetic, and/or hydrodissection fluid) to the tissue along the second or subsequent insertion path through openings 228 in the obturator 220 during the probing of step 1830. One of these openings 228 may be located at or comprise the most anterior portion of the anterior blunt tip 224 of the obturator 220, so that the delivered agent is the first element of the assembled minimally traumatic trocar 240 to contact tissues along the second insertion path. Alternatively, or in addition to this configuration, the obturator 220 may include one or more openings proximal to the anterior rounded tip (as shown in FIGS. 2B and 3A-E) that deliver the agent to tissues adjacent to the anterior rounded tip 224 and the tubular body 222 of the obturator 220 and tubular cannula body 202. The delivered agent effectively lubricates the passage of the assembled minimally traumatic trocar 240 by creating a fluid buffer around the assembled minimally traumatic trocar 240 and gently separating the various tissues encountered by the assembled minimally traumatic trocar 240 during probing along the second insertion path.

At decision diamond 1834, a determination is made as to whether additional doses of the particular agent or hydro-dissection fluid are required. A medical professional may determine to inject an additional dose, such as of hydrodissection fluid, when the initial administration of hydrodissection fluid fails to adequately ease insertion of the minimally traumatic trocar 240 to a desired length or depth along the second insertion path. In practice, an medical professional may inject a further dose of hydrodissection fluid through the atraumatic trocar 240 into the blocking tissue and/or surrounding tissue with the same syringe used to inject the first dose of hydrodissection fluid into the tissues of the second insertion path.

Upon injecting one or more doses of hydrodissection fluid, the method 1800 continues at step 1836, where the obturator 220 is removed from the cannula 200 and the incision 1302. In one embodiment, the cannula 200 is kept in position, while the obturator 220 is removed. The cannula 200 may be kept in position by holding the cannula handle 210 while the obturator handle is used to withdraw the obturator 220.

At step 1838, a medication pellet 104 is loaded into the interior passage of the cannula 200 through the medication slot 208. In one embodiment, the loaded medication pellet is pushed toward the anterior opening 204 at the anterior end of the cannula 200 with the obturator 220, but not through the anterior opening 204. In another embodiment, the loaded medication pellet is pushed toward the anterior opening 204 at the anterior end of the cannula 200 and through the anterior opening 204 into the subcutaneous tissue surrounding the second delivery site, and/or along the second insertion path (i.e. the second delivery area).

At decision diamond 1840, a next medication pellet may be loaded into the interior passage of the cannula 200 in the same fashion as the first medication. The next medication pellet 104 can be a second, third, fourth, fifth, sixth, etc. medication pellet depending on the number of previously loaded medication pellets. In one embodiment, when a next pellet is loaded into the interior passage of the cannula 200, the most recently loaded medication pellet is pushed toward the anterior opening 204 at the anterior end of the cannula 200 with the obturator 220. Any next or subsequently loaded medication pellets are pushed through the cannula 200 so that none of the previously loaded medication pellets are extruded through the anterior opening 204 at the anterior end of the cannula 200 and delivered to the second delivery area.

At step 1842, the desired number of medication pellets 104 have been loaded into the interior passage of the cannula 200, and the anterior blunt tip 224 of the obturator 220 is inserted into the posterior opening 206 of the cannula 200. The blunt tip 224 of the obturator 220 is passed through the interior passage of the cannula 200 to abut the most posterior loaded medication pellet 104 and push all pellets into a desired position. In one embodiment, the desired position for the medication pellets is as depicted in FIG. 12B, where the loaded pellets 104 pressed to abut one another and align with the cannula markings 214, as well as the anterior opening 204 of the cannula 200.

At step 1844, the loaded medication pellet(s) 104 are extruded through the anterior opening 204 of the cannula 200 and delivered to a second subcutaneous delivery area. In one embodiment, the cannula 200 is slowly removed from the incision 1302 as the obturator 220 is inserted further into the interior passage of the cannula 200. By slowly removing the cannula 200 during insertion of the obturator 220, the delivery site for each successive medication pellet is shifted closer to the incision 1302. Moving the delivery site 1306 of successive pellets allows the medication pellets to be delivered in a linear formation as in FIGS. 15 and 16, or a snaking, winding or "staggered" formation as in FIGS. 13 and 14, as opposed to the radial clump 130 of the prior art in FIG. 1D. Thus, simultaneous removal of the cannula 200 and insertion or depression of the obturator 220 forces successive medication pellets out of the cannula 200 into a delivery site that is unique for each medication pellet. In some embodiments, complete extrusion of the medication pellets results in full insertion of the obturator 220 into the interior passage of the cannula 200, such that the obturator 220 and cannula 200 are again assembled into the minimally traumatic trocar 240.

At step 1846, the obturator 220 and cannula 200, which may be assembled as the minimally traumatic trocar 240, are retracted along the insertion path toward the incision 1302. In one embodiment, at least one of the anterior rounded tip 224, an anterior portion of the cannula 200, or any combination thereof remains within the incision 1302 while most of the length of the tubular obturator body 222 and the tubular cannula body 202 are removed from the incision 1302. Leaving at least one of the anterior rounded tip 224, an anterior portion of the cannula 200, or any combination thereof remains within the incision 1302 allows the method 1800 to either terminate at the ensuing step 1828, or return to decision diamond 1826 and continue with the establishment of a third or next insertion path for reception of a third set of medication pellet(s).

Notably, whether the minimally traumatic trocar 240 was inserted along a linear path as in FIGS. 15 and 16, or a snaking path as in FIGS. 13 and 14, the corresponding minimally traumatic trocar 240 is removed directly, i.e. without any snaking, wiggling, or wagging, such that the removal of the minimally traumatic trocar 240 follows a linear or approximately linear path. Thus, no matter the type of insertion path, the minimally traumatic trocar 240 is retracted with a linear motion along a linear path. As described above, when the insertion path is non-linear, displaced tissue resumes its approximate original location and locks one or more delivered medication pellets in place in the subcutaneous tissue. When the insertion path is linear, tissue may still contract about the delivered medication pellet(s) to hold them in place, although the force of this holding action may be less than when a non-linear insertion path is used.

At step 1828, the cannula 200 or assembled minimally traumatic trocar 240 is removed from the incision 1302, the incision 1302 is closed and the method 1800 ends. The incision 1302 may be closed with stitches, medical glue, butterfly bandage, or similar bandaging means.

In further embodiments, the pellet dosage of a target compound, i.e. testosterone, estrogen, progesterone, is determined in relation to a baseline measurement of the target compound in the patient's blood stream. The baseline measurement is determined prior to delivery of medication pellets with minimal amounts of micro-trauma. The efficacy of the selected dosage is then determined by measuring the amount of the compound per volume, termed a compound level, in the patient's bloodstream at various time periods after subcutaneous insertion of the medication pellets. In various embodiments, the compound level is measured one week, one month, three months, and six months after pellet delivery with minimal amounts of micro-trauma. In other embodiments, the compound level is measured weekly, biweekly, or monthly. Later minimally traumatic pellet delivery doses are then adjusted, i.e. increased or decreased, depending on whether the compound levels resulting from a previous minimally traumatic delivery were higher or lower than desired.

In an exemplary embodiment, normal testosterone blood levels range from 400 to 1,200 nanograms/deciliter (ng/dl), but a patient's testosterone baseline level is measured at 50 ng/dl. One week after atraumatically delivering one 200 mg pellet of testosterone, the patient's testosterone level is measured at 60 ng/dl, one month after atraumatic delivery the patient's testosterone level is measured at 100 ng/dl, and three months after atraumatic delivery the patient's testosterone level is measured at 105 ng/dl. This feedback may suggest to a doctor or operator that a subsequent atraumatically delivered pellet dosage should be increase to two, three, four, or more 200 mg pellets. This method of baseline measurement, followed by post-delivery measurement accounts for the differences in patient body composition, activity level, and metabolism, which vary significantly and affect pellet dissolution into the blood stream.

The atraumatic trocar apparatus, system and method described above may be used to deliver medication pellets into subcutaneous tissue with little, minimal, or only micro-traumatic damage to the subcutaneous tissue. The inventor hypothesizes that the atraumatic insertion and subcutaneous delivery of medication pellets improves the absorption rate of the medication pellets over prior art trocar apparatuses by limiting or eliminating trauma, such as laceration to nerves, arterioles, venuoles, capillaries, or fat cell membrane punctures, which result in cellular death and may cause the formation of chronic collagenous scar tissue.

Further, the inventor hypothesizes that the minimally traumatic method of pushing aside and slipping past connective and fatty tissue with the rounded tip of the insertion obturator allows the connective and fatty tissue to move or pop back toward their original position as the trocar is removed from the insertion path and incision. As the connective and fatty tissue moves, slides, or pops back toward its original position, the connective and fatty tissues have the effect of locking or blocking the delivered medication pellets in place.

Further still, the inventor hypothesizes that the locking or blocking action of the connective and fatty tissue prevents or limits the likelihood that the delivered medication pellets are inadvertently extruded from the subcutaneous tissue because of pressure, a fall, or other stress.

The inventor further hypothesizes that the minimally traumatic insertion and subcutaneous delivery of medication pellets allows the incision made to insert the medication pellets to heal more quickly and decrease the likelihood that a subcutaneously delivered or inserted medication pellet is inadvertently extruded from the subcutaneous tissue because of pressure, a fall, or other stress.

Additionally, the inventor hypothesizes that the reduced inflammation caused by the minimally traumatic trocar apparatus and methods reduce the degree and incidence of scarring at the incision and insertion site. This reduced degree and incidence of scarring enables repeat dosing using the same insertion site.

The invasive, traumatic prior art methods of subcutaneous pellet insertion cause blood to pool around the traumatized delivery site due to local destruction of fatty tissue, creating pain, inflammation, higher incidences of infection, and a lubricated exit path along which inserted pellets are more likely to be extruded. In contrast, the presently disclosed systems and methods of minimally traumatic subcutaneous pellet delivery allows pellets to sit in a layer of fatty tissue with limited or minimal abnormal blood or lymph fluids surrounding the delivered pellets. The inflammation and/or pain caused by the traumatic prior art method of destroying fatty tissues is undesirable both because of pain's effect on the patient's psyche and because the size of the local inflammatory cytokine response creates a milieu that poorly dissolves medication pellets, or fails to dissolve medication pellets entirely. All of these issues are exacerbated for men, due in part to the larger doses required, with complications occurring in men up to 30 times more often than in women. Various studies have shown extrusion rates for prior art methods of ~1% up to 12%. The inventor hypothesizes that this minimally traumatic delivery allows the pellets to be recognized earlier by the body and absorbed more quickly, predictably, and deliberately as a result, and as compared to traumatic insertion. The minimally traumatic delivery triggers only a minor inflammatory cytokine response, sufficient to signal macrophages to selectively surrounding and dissolve inserted pellets. By reducing the concentration of cytokines at insertion sites as compared to prior art methods and apparatus, the minimally traumatic apparatus and methods yield an unexpectedly improved pellet absorption rate. To date, no pellets inserted with the minimally traumatic apparatus and methods described herein have been extruded, resulting in a greatly improved extrusion rate of 0%.

Additional benefits flow from the minimally traumatic design of the present invention. The absence of separate insertion and delivery obturators, as well as the absence of cutting trauma when using the minimally traumatic trocar, reduce the time and complexity of pellet insertion procedures significantly (~6 minutes for a minimally traumatic insertion compared to ~20 for the Biote™ traumatic procedure). This reduced procedure time and complexity enable non-surgeons to perform the minimally traumatic method, lowering costs to both patient and surgeon.

It is to be understood that the detailed description of illustrative embodiments are provided for illustrative purposes. Thus, the apparatus, system, kit and method presented above may evolve to benefit from the improved performance and lower cost of the future hardware components that meet the system and method requirements presented. The scope of the claims is not limited to these specific embodiments or examples. Therefore, various process limitations, elements, details, and uses can differ from those just described, or be expanded on or implemented using technologies or materials not yet commercially viable, and yet still be within the inventive concepts of the present disclosure. The scope of the invention is determined by the following claims and their legal equivalents.

What is claimed is:

1. A method for delivering a medication pellet through an incision to a delivery site within a subcutaneous tissue comprising:

receiving an obturator in a cannula, wherein the obturator includes an anterior rounded tip and a tubular obturator body, wherein the cannula includes a tubular cannula body having a smooth anterior surface and a medication slot disposed along the tubular cannula body, and wherein an inner diameter of the tubular cannula body is at least 3 millimeters (mm);

passing the obturator through the tubular cannula body so that the anterior rounded tip of the obturator extends past the smooth anterior surface of the tubular cannula body;

probing, with the cannula and the obturator, the incision into the subcutaneous tissue along a non-linear insertion path within the subcutaneous tissue;

removing the obturator from the tubular cannula body;

placing the medication pellet in the medication slot;

receiving, by the tubular cannula body having the medication pellet therein, the obturator;

passing, by the anterior rounded tip of the obturator, the medication pellet through the tubular cannula body so that the obturator pushes the medication pellet through the tubular cannula body and the medication pellet exits the tubular cannula body;

delivering, by passing the obturator through the tubular cannula body, the medication pellet; and aligning the medication pellet along the insertion path.

2. The method of claim 1 further including probing along the insertion path in a side-to-side pattern the cannula and the obturator.

3. The method of claim 1 wherein the cannula includes a cannula handle fixedly coupled to the cannula; and the obturator includes an obturator handle fixedly coupled to the obturator.

4. The method of claim 1 wherein the cannula includes a first coupling element;

wherein the obturator includes a second coupling element; and wherein the first coupling element and the second coupling element couple to one another when the obturator passes through the tubular cannula body so that the anterior rounded tip of the obturator extends past the smooth anterior surface of the tubular cannula body.

5. The method of claim 4 wherein the second coupling element includes at least one tab, and the first coupling element includes at least one notch.

6. The method of claim 1 further comprising probing with the cannula and obturator the incision into the subcutaneous tissue along the insertion path so that the anterior rounded tip of the obturator precedes the cannula.

7. The method of claim 1 further comprising, inserting a hydrodissection microcannula into the incision; and injecting a hydrodissecting liquid along the insertion path before receiving the obturator and the cannula.

8. The method of claim 7 wherein the hydrodissecting fluid includes at least one of a lidocaine compound, a epinephrine compound, and an antifibrinolytic compound.

9. A method for delivering a medication pellet through an incision to a delivery site within a subcutaneous tissue, the method comprising:

inserting a trocar apparatus through the incision to the delivery site within the subcutaneous tissue, wherein the trocar apparatus includes, a cannula with a tubular cannula body, a smooth anterior surface, and a medication slot disposed along the tubular cannula body that receives the medication pellet, and an obturator that includes a tubular obturator body and an anterior rounded tip, wherein the obturator is received within the tubular cannula body, and extend through the tubular cannula body so that the anterior rounded tip of the obturator extends past the smooth anterior surface of the tubular cannula body;

probing, with the trocar apparatus, the incision along a non-linear insertion path within the subcutaneous tissue;

removing the obturator from the cannula:

placing the medication pellet in the medication slot;

receiving, by the tubular cannula body having the medication pellet therein, the obturator; and passing, by the anterior rounded tip, the medication pellet through the tubular cannula body so that the anterior rounded tip pushes the medication pellet through the tubular cannula body and the medication pellet exit the tubular cannula body into the subcutaneous tissue;

delivering, by passing the obturator through the tubular cannula body, the medication pellet; and aligning the medication pellet along the insertion path.

10. The method of claim 9 further includes probing, with the trocar apparatus, in a side-to-side pattern.

11. The method of claim 9 wherein the cannula further includes a cannula handle fixedly coupled to the cannula; and the obturator further includes an obturator handle fixedly coupled to the obturator.

12. The method of claim 9 wherein the cannula includes a first coupling element; wherein the obturator includes a second coupling element; and wherein the first coupling element and the second coupling element couple to one another when the obturator passes through the tubular cannula body so that the anterior rounded tip of the obturator extends past the smooth anterior surface of the tubular cannula body.

13. The method of claim 12 wherein the second coupling element includes at least one tab, and the first coupling element includes at least one notch.

14. The method of claim 9 further comprising probing with the trocar apparatus the incision into the subcutaneous tissue along the insertion path so that the anterior rounded tip of the obturator precedes the cannula.

15. A method for delivering two or more medication pellets through an incision to a delivery site within a subcutaneous tissue comprising:

receiving an obturator in a cannula, wherein the obturator includes an anterior rounded tip and a tubular obturator body, wherein the cannula includes a tubular cannula body having an anterior end, a posterior end, and a medication slot disposed along the tubular cannula body;

passing the obturator through the tubular cannula body so that the anterior rounded tip of the obturator extends past the anterior end of the tubular cannula body;

probing, with the cannula and the obturator, the incision into the subcutaneous tissue along a non-linear insertion path within the subcutaneous tissue;

removing the obturator from the tubular cannula body;

placing the two or more medication pellets in the medication slot;

receiving, by the tubular cannula body having the two or more medication pellets therein, the obturator;

passing, by the anterior rounded tip of the obturator, the two or more medication pellets through the tubular cannula body so that the obturator pushes the two or more medication pellets through the tubular cannula body and the two or more medication pellets exit the anterior end of the tubular cannula body;

delivering, by passing the obturator through the tubular cannula body, the two or more medication pellets; and aligning the two or more medication pellets along the non-linear insertion path.

16. The method of claim 15 further including probing along the insertion path in a side-to-side pattern the cannula and the obturator.

17. The method of claim 15 wherein the cannula includes first coupling element;

wherein the obturator includes a second coupling element; and wherein the first coupling element and the second coupling element couple to one another when the obturator passes through the tubular cannula body so that the anterior rounded tip of the obturator extends past the anterior end of the tubular cannula body.

18. The method of claim 17 wherein the second coupling element includes at least one tab, and the first coupling element includes at least one notch.

19. The method of claim 15 wherein a surface of the anterior end of the tubular cannula body includes a smooth edge.

20. The method of claim 15 further comprising probing with the cannula and obturator the incision into the subcutaneous tissue along the insertion path so that the anterior rounded tip of the obturator precedes the cannula.

* * * * *